(12) United States Patent
Wang et al.

(10) Patent No.: US 6,528,701 B1
(45) Date of Patent: Mar. 4, 2003

(54) RICE UBIQUITIN-DERIVED PROMOTERS

(75) Inventors: Jianlin Wang, Baton Rouge, LA (US); James H. Oard, Baton Rouge, LA (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 0 days.

(21) Appl. No.: 09/516,277

(22) Filed: Feb. 29, 2000

Related U.S. Application Data
(60) Provisional application No. 60/198,241, filed on Mar. 2, 1999, now abandoned.

(51) Int. Cl.$^7$ .......................... C12N 15/09; C12N 15/29; C12N 15/82; A01H 5/00
(52) U.S. Cl. .................. 800/278; 800/298; 800/320; 800/320.2; 800/279; 435/419; 435/468; 435/320.1; 536/23.6; 536/24.1
(58) Field of Search ................................. 800/278, 320, 800/320.2, 298, 279; 435/419, 468, 320.1; 536/23.6, 24.1

(56) References Cited

U.S. PATENT DOCUMENTS

| | | | |
|---|---|---|---|
| 5,510,474 A | 4/1996 | Quail et al. | 536/24.1 |
| 5,614,399 A | 3/1997 | Quail et al. | 435/172.3 |
| 5,723,757 A | 3/1998 | Rocha-Sosa et al. | 800/205 |
| 5,723,765 A | 3/1998 | Oliver et al. | 800/205 |
| 5,750,866 A | 5/1998 | Dietrich et al. | 800/205 |
| 5,773,705 A | 6/1998 | Vierstra et al. | 800/250 |

OTHER PUBLICATIONS

Binet et al., "Analysis of a sunflower polyubiquitin promoter by transient expression," Plant Science, vol. 79, pp. 87–94 (1991).
Bond et al., Ubiquitin is a Heat Shock Protein in Chicken Embryo Fibroblasts. Molecular and Cellular Biology, vol. 5, No. 5, pp. 949–956.
Callis et al., "Ubiquitin Extension Proteins of *Arabidopsis thaliana*," The Journal of Biological Chemistry, vol. 265, No. 21, pp. 12486–12493 (1990).
Callis et al., "Ubiquitin and Ubiquitin Genes in Higher Plants," Oxford Surveys of Plant Molecular & Cell Biology, vol. 6, pp. 1–30 (1989).
Christensen et al., "Maize polyubiquitin genes: structure, thermal perturbation of expression and transcript splicing, and promoter activity following transfer to protoplasts by electroporation," Plant Molecular Biology, vol. 18, pp. 675–689 (1992).
Christensen et al., "Ubiquitin promoter–based vectors for high–level expression of selectable and/or screenable marker genes in monocotyledonous plants," Transgenic Research, vol. 5, pp. 213–218 (1996).
Garbarino et al., "Expression of stress–responsive ubiquitin genes in potato tubers," Plant Molecular Biology, vol. 20, pp. 235–244 (1992).
Genschick et al., "Structure and promoter activity of a stress and developmentally regulated polyubiquitin–encoding gene of *Nicotiana tabacum*," Gene, vol. 148, pp. 195–202 (1994).
Guerrero et al., "Promoter sequences from a maize pollen–specific gene direct tissue–specific transcription in tobacco," Mol. Gen. Genet, vol. 224, pp. 161–168 (1990).
Hoffman et al., "Isolation and characterization of tomato cDNA and genomic clones encoding the ubiquitin gene ubi3," Plant Molecular Biology, vol. 17, pp. 1189–1201 (1991).
Kawalleck et al., "Polyubiquitin gene expression and structural properties of the ubi4–2 gene in *Petroselinum crispum*," Plant Molecular Biology, vol. 21, pp. 673–684 (1993).
Khoury et al., Enhancer Elements. Cell, vol. 33, pp. 313–314 (1983).
McElroy et al., "Isolation of an Efficient Actin Promoter for Use in Rice Transformation," The Plant Cell, vol. 2, pp. 163–171 (1990).
Toki et al., "Expression of a Maize Ubiquitin Gene Promoter–bar Chimeric Gene in Transgenic Rice Plants," Plant Physiol, vol. 100, pp. 1503–1507 (1992).
Viersta, R.D., "Proteolysis in plants: mechanisms and functions," Plant Molecular Biology, vol. 32, pp. 275–302 (1996).
Wang et al., "Isolation and Characterization of Rice Ubiquitin Genes," in Proceedings of Twenty–Seventh Rice Technical Working Group, in Reno, Nevada on Mar. 1–4, 1998, proceedings published Jan. 2000.
Wang et al., "Structure, Expression and Promoter Activity of Two Polyubiquitin Genes From Rice (*Orya sativa* L.)," Abstract, Plant & Animal Genome VIII, The International Conference on the Status of Plant Animal Genome Research, San Diego, California, Jan. 9–12, 2000.
Zhang et al., "Efficient regeneration of transgenic plants from rice protoplasts and correctly regulated expression of the foreign gene in the plants," Theor. App. Genet., vol. 76, pp. 835–840 (1988).

*Primary Examiner*—Phuong T. Bui
*Assistant Examiner*—Medina A. Ibrahim
(74) *Attorney, Agent, or Firm*—Bonnie J. Davis

(57) ABSTRACT

Four rice ubiquitin genes have been sequenced, including the promoter region. Among the four promoters, two belong to a class known as polyubiquitin genes and two to the class of ubiquitin fusion genes. The two polyubiquitin genes both comprise of 6 ubiquitin-monomers in the coding region. Promoters isolated from the polyubiquitin genes were shown to drive strong constitutive expression in transformed rice plants. Expression of the one polyubiquitin gene was induced by heat-shock treatment. The ubiquitin promoters can be used to drive expression of structural genes including but not limited to genes for herbicide resistance, resistance to pests, and tolerance to drought or other adverse environmental conditions.

12 Claims, 10 Drawing Sheets

```
        Sal I
   1   GTCGACCTGATGATTATTTTGTTGATCATGATTTTCTTTTGGCTATTTGA
  51   TTTTTTGAAAGATATTTTTTTCCCTGGGAAGACACCTATGGGACGAAGAT
 101   ATTATGTTATATATATATATATATATATATATATATATATATATATATAT
 151   ATATATATATATATCACATCAGTCTCTGCACAAAGTGCATCCTGGGCT
 201   GCTTCAATTATAAAGCCCCATTCACCACATTTGCGAGATAGTCGAAAAGC
 251   ACCATCAATATTGAGCTTCAGGTATTTTGGTTGTGTTGTGGTTGGATTG
 301   AGTCCGATATATACCAAATCAATATAATTCACTACGGAATATACCATAGC
 351   CATCACAACTTTATTAATTTTGGTAGCTTAAGATGGTATATATAATAACC
 401   AATTAACAACTGATTCTAATTTTACTACGGCCCAGTATCTACCAATACAA
 451   AACAACGAGTATGTTTTCTTCCGTCGTAATCGTACACAGTACAAAAAAAC
 501   CTGGCCAGCCTTTCTTGGGCTGGGGCTCTCTTTCGAAAGGTCACAAAACG
 551   TACACGGCAGTAACGCCCTTCGCTGCGTGTTAACGGCCACCAACCCCGCC
 601   GTGACGAAACGGCATCAGCTTTCCACCTCCTCGATATCTCCGCGGCGCCG
 651   TCTGGACCCGCCCCCTTTCCGTTCCTTTCTTTCCTTCTCGCGTTTGCGTG
 701   GTGGGGACGGACTCCCCAAACCGCCTCTCCCTCTCTTTATTTGTCTATAT
 751   TCTCACTGGGCCCCACCCACCGCACCCCTGGGCCCACTCACGAGTCCCCC
 801   CCTCCCGACCTATAAATACCCCACCCCCTCCTCGCCTCTTCCTCCATCAA
 851   TCGAATCCCCAAAATCGCAGAGAAAAAAAATCTCCCCTCGAAGCGAAGC
 901   GTCGAATCGCCTTCTCAAGgtatgcgattttctgatcctctccgttcctc
 951   gcgtttgatttgatttcccggcctgttcgtgattgtgagatgttgtggtt
1001   agtctccgttttgcgatctgtggtagatttgaacagggttagatggggtt
1051   cgcgtggtatgctggatctgtgattatgagcgatgctgaacgtggtccaa
1101   gtattgattggttcggatctagaagtagaagtagaactgtgctagggttg
1151   tgatttgttccgatctgttcaatcagtaggatttagtctctgttttctc
1201   gttgagccaagtagcagcgtcaggtatattttgcttaggttgttttgat
1251   tcagtccctctagttgcatagattctactctgttcatgtttaatctaagg
1301   gctgcgtcttgttgattagtgattacatagcatagctgtcaggatatttt
1351   acttgcttatgcctatcttatcaactgttgcacctgtaaattctagccta
1401   tgttaattaacctgccttatgtgctctcgggatagtgctagtagttattg
1451   aatcagtttgccgatggaattctagtagttcatagacctgcagattattt
1501   ttgtgaactcgagcacggtgcgtctctctatttgttaggtcactgttgg
1551   tgttgataggtacactgatgttattgtggtttagatcgtgtatctaacat
1601   attggaataatttgattgactgatttctgctgtacttgcttggtattgtt
1651   ataatttcatgttcatagttgctgaccatgcttcggtaattgtgtgtgca
                                                  Xho I
1701   gATGCAGATCTTTGTGAAGACCCTCACCGGCAAGACCATCACCCTCGAGG
        M  Q  I  F  V  K  T  L  T  G  K  T  I  T  L  E  V
1751   TTGAGTCCTCGGACACCATTGACAATGTCAAGGCCAAGATCCAGGACAAG
        E  S  S  D  T  I  D  N  V  K  A  K  I  Q  D  K
```

FIG. 1-A

```
1801  GAGGGCATCCCCCCGGACCAGCAGCGTCTCATCTTCGCTGGCAAGCAGCT
       E  G  I  P  P  D  Q  Q  R  L  I  F  A  G  K  Q  L
1851  TGAGGATGGCCGCACCCTGGCCGACTACAACATCCAGAAGGAGTCCACCC
       E  D  G  R  T  L  A  D  Y  N  I  Q  K  E  S  T  L
1901  TCCACCTTGTGCTCAGGCTCAGGGGAGGCATGCAGATCTTCGTCAAGACC
       H  L  V  L  R  L  R  G  G  M  Q  I  F  V  K  T
1951  TTGACTGGCAAGACCATCACCCTTGAGGTCGAGTCGTCTGACACCATTGA
       L  T  G  K  T  I  T  L  E  V  E  S  S  D  T  I  D
2001  CAATGTCAAGGCCAAGATCCAGGACAAGGAGGGCATCCCCCCGGACCAGC
       N  V  K  A  K  I  Q  D  K  E  G  I  P  P  D  Q  Q
2051  AGCGTCTCATCTTCGCTGGCAAGCAGCTTGAGGATGGCCGCACCCTGGCT
       R  L  I  F  A  G  K  Q  L  E  D  G  R  T  L  A
2101  GACTACAACATCCAGAAGGAGTCCACCCTCCACCTTGTGCTCAGGCTCAG
       D  Y  N  I  Q  K  E  S  T  L  H  L  V  L  R  L  R
2151  GGGAGGCATGCAGATCTTCGTCAAGACCTTGACTGGCAAGACCATCACCC
       G  G  M  Q  I  F  V  K  T  L  T  G  K  T  I  T  L
2201  TCGAGGTCGAGTCGTCTGACACCATTGACAATGTCAAGGCCAAGATCCAG
       E  V  E  S  S  D  T  I  D  N  V  K  A  K  I  Q
2251  GACAAGGAGGGCATCCCCCCAGACCAGCAGCGTCTCATCTTCGCCGGCAA
       D  K  E  G  I  P  P  D  Q  Q  R  L  I  F  A  G  K
2301  GCAGCTGGAGGATGGCCGCACCCTTGCTGACTACAACATCCAGAAGGAGT
       Q  L  E  D  G  R  T  L  A  D  Y  N  I  Q  K  E  S
2351  CCACCCTCCACCTTGTGCTCAGGCTCAGGGGAGGTATGCAGATCTTCGTC
       T  L  H  L  V  L  R  L  R  G  G  M  Q  I  F  V
2401  AAGACCCTGACCGGCAAGACCATCACCCTCGAGGTCGAGTCCTCGGACAC
       K  T  L  T  G  K  T  I  T  L  E  V  E  S  S  D  T
2451  GATCGACAATGTGAAAGCCAAGATCCAGGACAAGGAGGGCATCCCCCCGG
       I  D  N  V  K  A  K  I  Q  D  K  E  G  I  P  P  D
2501  ACCAGCAGCGTCTCATCTTTGCTGGCAAGCAGCTGGAGGATGGCCGCACC
       Q  Q  R  L  I  F  A  G  K  Q  L  E  D  G  R  T
2551  CTTGCCGACTACAACATCCAGAAGGAGTCCACCCTCCACCTTGTGCTCAG
       L  A  D  Y  N  I  Q  K  E  S  T  L  H  L  V  L  R
2601  GCTCAGGGGTGGTATGCAGATCTTCGTCAAGACCCTGACCGGCAAGACCA
       L  R  G  G  M  Q  I  F  V  K  T  L  T  G  K  T  I
2651  TCACGCTTGAGGTCGAGTCCTCGGACACGATCGACAATGTGAAGGCCAAG
       T  L  E  V  E  S  S  D  T  I  D  N  V  K  A  K
2701  ATCCAGGACAAGGAGGGTATCCCCCCGGACCAGCAGCGTCTCATCTTCGC
       I  Q  D  K  E  G  I  P  P  D  Q  Q  R  L  I  F  A
```

FIG. 1-B

```
2751  CGGCAAGCAGCTTGAGGATGGCCGCACCTTGGCTGACTACAACATCCAGA
       G  K  Q  L  E  D  G  R  T  L  A  D  Y  N  I  Q  K
2801  AGGAGTCCACCCTTCACCTGGTTCTCAGGCTCAGGGGTGGGATGCAGATC
       E  S  T  L  H  L  V  L  R  L  R  G  G  M  Q  I
2851  TTCGTGAAGACCCTGACTGGCAAGACCATTACCCTTGAGGTTGAGTCGTC
       F  V  K  T  L  T  G  K  T  I  T  L  E  V  E  S  S
2901  CGACACTATTGACAACGTGAAGGCGAAGATCCAGGACAAGGAGGGCATCC
       D  T  I  D  N  V  K  A  K  I  Q  D  K  E  G  I  P
2951  CCCCGGACCAGCAGCGTCTGATCTTTGCTGGTAAGCAGCTTGAGGATGGC
       P  D  Q  Q  R  L  I  F  A  G  K  Q  L  E  D  G
3001  CGCACCTTGGCGGATTACAACATCCAGAAGGAGTCCACACTCCACCTGGT
       R  T  L  A  D  Y  N  I  Q  K  E  S  T  L  H  L  V
3051  TCTGCGCCTCCGTGGTGGCCAGTAAGTCCTCAGCCATGGAGCTGCTGCTG
       L  R  L  R  G  G  Q  *
3101  TTCTAGGGTTCACAAGTCTGCCTATTGTCTCCCAATGGAGCTATGGTTGT
3151  CTGGTCTGGTCCTTGGTCGTGTCCCGTTTCATTG
```

FIG. 1-C

```
        Pst I
1       CTGCAGAAATGCAAATTTCATAAAACAAACTACTAGTACTGTTTGTTCAT
51      TGGTCTTATCCAAAACTTAGCCACTGCAACAAGTTCTTGAACCTTAGCAC
101     AATCATATTGTGCATGCACTTGTTTATTGCAAAGAATGGTGCGTAGGGAA
151     CACGCATGATTTTTGAATTGCTGGCACATAATTTTATCATTAGAAACTGG
201     AATGCAACATGTACCCTTTGTCATGGTTTCTTTCCGAGACATTGCACTGT
251     TTTTTTTAATCCTATCATTATCATAATGCCAAGAACTGGTCACCAACCAG
301     CATTTTGCATCATGGTTAGTTGAGCTGTCCCCATGTATCAATAGGTGCAT
351     TGTATTGGTCCAAAATATAAATGCAGTGGATGCAACCTATCTCATGGCCG
401     TCAACAAAAGAAATCAAAAGGGAAATGCACCATCTTATATCTCCAGTTTA
451     TATGAACAGATTGGATAAGATCATAAGATCAAGTGGTTTATATTATTTTG
501     AGGAATATAACATGGATTCATCCTAATCACTCGTCTAGGCAGTATGTGTA
551     TTCATGATGGATATGGTACTATACTACGGAGTTTTTTCTTCACAAAATAA
601     CCTGTTATTTGACCTCCAACCAAACACGAATTATACCAAAAATTGGGTT
651     ATTTCATCTATAGTACAACTCTATTATAAACATGCAGTAAATTATCCTAC
701     ACATATACCAAAATTCAAGTGTAATAATCCTAATACACAGACTTAAAAAT
751     CAAACTATTTCCTTTTTAAGATATGGAAAACCATTTTTTTAACGGAAGGA
801     AAACAAATTCGGGTCAAGGCGGAAGCCAGCGCGCCACCCCACGTCAGCGA
851     ATACGGAGGCGCGGGGTTGACGGCGTCACCCGGTCCTAACGGCGACCAAC
901     AAACCAGCCAGAAGAAATTACAGTAAAAAAAGTAAATTGCACTTTGACC
951     CACCTTTTATTACCCAAAGTTTCAATTTGGACCACCCTTAAACCTATCTT
1001    TTCAAATTGGGCCGGGTTGTGGTTTGGACTACCATGAACAACTTTTCGTC
1051    ATGTCTAACTTCCCTTTCGGCAAACATATGAACCATATATAGAGGAGATC
1101    GGCCGTATACTAGAGCTGATGTGTTTAAGGTCGTTGATTGCACGAGAAAA
1151    AAAAATCCAAATCGCAACAATAGCAAATTTATCTAGTTCAAAGTGAAAAG
1201    ATATGTTTAAAGGTAGTCCAAAGTAAAACTTAGGGGCTGTTTGGTTCCCA
1251    GCCATACTTTACCATTACTTGCCAACAAAAGTTGCCACACCTTGTCTAAG
1301    GTGAGGTGATCAAATTGTTAGCCACAACTTACTAAGCCTAAGGGAATCTT
1351    GCCACACTTTTTTGAGCCATTGACACGTGGGACTTAATTTGTTAGAGGGA
1401    AATCTTGCCACAACTGTGGCTACAACCAAACACCTGTCAAATTTGCCTAA
1451    CCTTAGGCGTGGCAAACTGTGGCAAAGTGTGGCTTACAACCAAACACACC
1501    CTTAGATAATAAAATGTGGTCCAAAGCGTAATTCACTAAAAAAAAATCAA
1551    CGAGACGTGTACCAAACGGAGACAAACGGCATCTTCTCGAAATTTCCCAA
1601    CCGCTGGCTGGCCCGCCTCGTCTTCCCGGAAACCGCGGTGGTTTCAGCGT
1651    GGCGGATTCTCCAAGCAGACGGAGACGTCACGGCACGGACTCCTCCCACC
1701    ACCCAACCGCCATAAATACCAGCCCCCTCATCTCCTCTCCTCGCATCAGC
1751    TCCACCCCCGAAAATTTCTCCCCAATCTCGCGAGGCTCTCGTCGTCGAA
1801    TCGAATCCTCTCGCGTCCTCAAGgtacgctgcttctcctctcctcgcttc
1851    gtttcgattcgatttcggacgggtgaggttgttttgttgctagatccgat
```

FIG. 2-A

```
1901  tggtggttagggttgtcgatgtgattatcgtgagatgtttaggggttgta
1951  gatctgatggttgtgatttgggcacggttggttcgataggtggaatcgtg
2001  gttaggttttgggattggatgttggttctgatgattgggggaattttta
2051  cggttagatgaattgttggatgattcgattggggaaatcggtgtagatct
2101  gttggggaattgtggaactagtcatgcctgagtgattggtgcgatttgta
2151  gcgtgttccatctagtaggccttgttgcgagcatgttcagatctactgtt
2201  ccgctcttgattgagttattggtgccatgggtgggtgcaaacacaggctg
2251  caatatgttatatctgttttgtgtttgatgtagatctgtagggtagttct
2301  tcttagacatggttcaattatgtagcttgtcgtttcgatttgatgctcat
2351  atgttcacagattagataatgatgaactcttttaattaattgtcaatggt
2401  aaataggaagtcttatcgctatatctgtcataatgatctcatgttactat
2451  ctgccagtaatttatgctaagcactatattagaatatcatgttacaatct
2501  gtagtaatatcatgttacaatctgtagttcatctatataatctattgtgg
2551  taatttcttttactatctgtgtgaagattattgccactagttcattcta
2601  cttatttctgaagttcaggatacgtgtgctgttactacctatctgaatac
2651  atgtgtgatgtgcctgttactatctttttgaatacatgtatgttctgttg
2701  gaatatgtttgctgtttgatccgttgttgtgtccttaatcttgtgctagt
2751  tcttaccctatctgtttggtgattatttcttgcagATGCAGATCTTTGTG
                                        XhoI    M  Q  I  F  V
2801  AAGACATTGACCGGCAAGACTATCACCCTCGAGGTGGAGTCCTCTGACAC
       K  T  L  T  G  K  T  I  T  L  E  V  E  S  S  D  T
2851  CATCGATAATGTCAAGGCTAAGATCCAAGATAAGGAGGGCATCCCCCCGG
       I  D  N  V  K  A  K  I  Q  D  K  E  G  I  P  P  D
2901  ACCAGCAGCGTCTCATCTTCGCTGGCAAGCAGCTGGAGGATGGCAGGACC
       Q  Q  R  L  I  F  A  G  K  Q  L  E  D  G  R  T
2951  CTTGCTGACTACAACATCCAGAAGGAGTCGACCCTTCACCTTGTCCTCCG
       L  A  D  Y  N  I  Q  K  E  S  T  L  H  L  V  L  R
3001  CCTCCGTGGTGGCATGCAGATCTTTGTCAAGACTCTGACCGGCAAGACTA
       L  R  G  G  M  Q  I  F  V  K  T  L  T  G  K  T  I
3051  TCACCCTTGAGGTGGAGTCTTCTGACACCATCGACAACGTCAAGGCCAAG
       T  L  E  V  E  S  S  D  T  I  D  N  V  K  A  K
3101  ATCCAGGACAAAGAGGGCATCCCCCCAGACCAGCAGCGTCTCATCTTCGC
       I  Q  D  K  E  G  I  P  P  D  Q  Q  R  L  I  F  A
3151  CGGCAAGCAGCTGGAGGATGGCAGGACCCTTGCTGACTACAACATCCAGA
       G  K  Q  L  E  D  G  R  T  L  A  D  Y  N  I  Q  K
3201  AGGAGTCCACCCTCCACCTTGTCCTCCGCCTCCGTGGTGGCATGCAGATC
       E  S  T  L  H  L  V  L  R  L  R  G  G  M  Q  I
3251  TTTGTCAAGACACTGACCGGCAAGACCATCACCCTCGAGGTGGAATCTTC
       F  V  K  T  L  T  G  K  T  I  T  L  E  V  E  S  S
```

FIG. 2-B

```
3301  TGACACCATCGACAACGTCAAGGCCAAGATCCAGGACAAGGAGGGCATTC
       D  T  I  D  N  V  K  A  K  I  Q  D  K  E  G  I  P
3351  CCCCGGACCAGCAGCGTCTCATCTTTGCCGGCAAGCAGCTTGAGGACGGC
       P  D  Q  Q  R  L  I  F  A  G  K  Q  L  E  D  G
3401  AGGACCCTTGCTGACTACAACATCCAGAAGGAGTCAACGCTTCACCTTGT
       R  T  L  A  D  Y  N  I  Q  K  E  S  T  L  H  L  V
3451  CCTCCGTCTCAGGGGAGGCATGCAAATCTTCGTGAAGACTCTGACCGGCA
       L  R  L  R  G  G  M  Q  I  F  V  K  T  L  T  G  K
3501  AGACCATCACCCTCGAGGTGGAGTCTTCTGATACCATCGACAATGTCAAG
       T  I  T  L  E  V  E  S  S  D  T  I  D  N  V  K
3551  GCCAAGATCCAGGACAAGGAGGGCATTCCCCCGGACCAGCAGCGCCTCAT
       A  K  I  Q  D  K  E  G  I  P  P  D  Q  Q  R  L  I
3601  CTTTGCTGGCAAGCAGCTGGAGGATGGCAGGACCCTTGCTGACTACAACA
       F  A  G  K  Q  L  E  D  G  R  T  L  A  D  Y  N  I
3651  TCCAGAAGGAGTCCACCCTCCACCTTGTGCTCCGCCTTCGTGGTGGTATG
       Q  K  E  S  T  L  H  L  V  L  R  L  R  G  G  M
3701  CAGATCTTTGTCAAGACCCTCACAGGCAAGACCATCACCCTGGAGGTTGA
       Q  I  F  V  K  T  L  T  G  K  T  I  T  L  E  V  E
3751  GAGCTCGGACACCATCGACAACGTCAAGGCCAAGATCCAGGACAAGGAGG
       S  S  D  T  I  D  N  V  K  A  K  I  Q  D  K  E  G
3801  GCATCCCCCCAGACCAGCAGCGTCTCATCTTCGCCGGCAAGCAGCTCGAG
       I  P  P  D  Q  Q  R  L  I  F  A  G  K  Q  L  E
3851  GATGGCCGCACCCTTGCCGACTACAACATCCAGAAGGAGTCTACCCTCCA
       D  G  R  T  L  A  D  Y  N  I  Q  K  E  S  T  L  H
3901  CCTGGTGCTTCGTCTCCGTGGTGGTATGCAGATCTTCGTGAAGACCTTGA
       L  V  L  R  L  R  G  G  M  Q  I  F  V  K  T  L  T
3951  CTGGGAAGACCATCACTTTGGAGGTTGAGAGCTCCGACACCATTGATAAT
       G  K  T  I  T  L  E  V  E  S  S  D  T  I  D  N
4001  GTGAAGGCCAAGATCCAGGACAAGGAGGGGATTCCCCCAGACCAGCAGCG
       V  K  A  K  I  Q  D  K  E  G  I  P  P  D  Q  Q  R
4051  TCTGATCTTCGCTGGCAAGCAGCTGGAGGATGGACGCACCCTCGCCGACT
       L  I  F  A  G  K  Q  L  E  D  G  R  T  L  A  D  Y
4101  ACAACATCCAGAAGGAGTCCACCCTCCACCTGGTGCTCCGCCTCCGTGGT
       N  I  Q  K  E  S  T  L  H  L  V  L  R  L  R  G
      GGTCAGTAATCAGCCAGTTTGGTGGAGCTGCCGATGTGCCTGGTCATCCC
       G  Q  *
4201  GAGCCTCTGTTCGTCAAGTATTTGTGGTGCTGATGTCTACTTGTGTCTGG
4251  TTTAATGGACCATCGAGTCCGTATGATATGTTAGTTTTATGAAACAGTTT
4301  CCTGTGGGACAGCAGTATGCTTTATGAATAAGTTGGATTTGAACCTAAAT
4351  ATGTGCTCAATTTGCTCATTTGCATCTCATTCCTGTTGATGTTTTATTTG
4401   AGTTGCAAGTTTGAAAATGCTGCATATTCTTATTAAACGGCA
```

FIG. 2-C

```
         HindIII
   1     AAGCTTTGCTCCGTGTCTGCTTGGGCCATATACACGGACCAGCCCAATAG
  51     CCAGAAGCCTGTAGCTCTCCATGGGCCCGTACTCGTGCCACGTGTCAATC
 101     CTGTGGTTCGGTTTCGTGGCGGTTGCGTTTCCTCCTCTCTTTTCTTTT
 151     TCATCTTTTTTTTTTCTTACGACATTTATAGGTTTCGTAGCGGCTGCGTT
 201     TCCTATTTTCCTTTTCTTTTTCTATTTATTTTTATGGGATATTCGCTTTC
 251     GTGGCGGCTGCGTTTCCTCGCCCATATATAAGAGCGGGTGACCACGACTG
 301     CGGCGCGGCGCACCACTCCACCACCACCACCACCACTCCACCGATCGGCG
                                              BglII
 351     AGAGCGCGGGGAGATCGTTCGACGGCGGCAAGATGCAGATCTTCGTGAAG
                                         M   Q   I   F   V   K
 401     ACGCTGACGGGGAAGACGATCACGCTGGAGGTGGAGAGCAGCGACACCAT
          T   L   T   G   K   T   I   T   L   E   V   E   S   S   D   T   I
 451     CGACAACGTCAAGGCCAAGATCCAGGACAAGGAAGgtatgctcgcaccgg
          D   N   V   K   A   K   I   Q   D   K   E   G
 501     ccatggtcgccgactcgccgtctctccattcctagccctccccgttctcg
 551     ctgacctgcattgattgctgctttgtttggtgtgctcgatatgctgatat
 601     gttactgtgtttgtgtgcaaatctgtgggtttagtggagtttatgcgctg
 651     tggatatagcagttgcaagttttgtgggtttagtggaatactgagcaaa
 701     atgcgtaaactctagtagtatcacccatccaatgttgctgcttttctacc
 751     attttttagatctgtaacagagtagatccatcttgaaaagcgtataaaa
 801     gcccaaaaccttccgattgaatagttcctttccaatttctctggaggcga
 851     ttttttttttttataactgtcacgctatactgcacggttaactagatctaa
 901     aaggtcccctgttttcctgttacaataagcaaaaaagtatgttgtttta
 951     taatctgattcgaactacttgaatagattcctaaaacgttctgtatcctt
1001     ttacatgctgtattgatttgatcctccggtagtgttaatttcatatcacg
1051     ctctgctaagctggaaattgttgaatccgtgtgtgcgcatggtcgaatct
1101     ctctgctgtttaagctgatgaactgtatccatctctgcacaacccgtaca
1151     gGTATCCCGCCGGACCAGCAGCGCCTCATCTTCGCCGGGAAGCAGCTGGA
           I   P   P   D   Q   Q   R   L   I   F   A   G   K   Q   L   E
1201     AGACGGCCGCACCCTGGCCGACTACAACATCCAGAAGGAGTCGACGCTGC
          D   G   R   T   L   A   D   Y   N   I   Q   K   E   S   T   L   H
1251     ACCTGGTGCTCCGCCTCCGCGGCGGCAGCAGGGGCGGCTACACCATCCAG
          L   V   L   R   L   R   G   G
1301     GAGCCCACCCTCCGGGCTCTTGCGCTCAAGTACAGAGAGAAGAAGAAGGT
1351     CTGCCGCAAGTACGAACTCACGCACGCCCCCGCCCGCCCGCACCTTGATT
1401     CCAGATGATACTAGCTTTGCATCCGCGGCTAACATGAACTGATTTGATTT
1451     CAACCCTGTTCCATCTCCTAATGCAGGTGCTATGCACGCCTTCCCATCAG
1501     GTCTCACCACTGCCGCAAGAAGAAGTGTGGCCACAGCAAGGAGGTGAGCA
1551     TTTCTAAAGTTCCTCTTCGTATGTTAACACACCATTGTTCATGTTCTTGG
1601     CTTTGCTTTGGTCTGAATGCTGGAGATGAATTTTTCTTAGATAGTTGTCA
1651     TACTCCTGTACTTTGTATTGGAAATTCGAAATCGTCATTGGTTGCCTCCG
1701     TGTGCGCTTGTCACGGATTTGGAAATTTGGATAGAGTCGCATCAGTTTGA
1751     ACACCAATTCAGTTCAGTGGTTTGCCCTTTGAATTGTGTTTATTCTAGTG
1801     ATTACTGTGTTCTGCATCGGTTGCAATACACGCTGTACAGTTTTTT
```

FIG. 3

```
             HindIII
   1    AAGCTTGTCTGTCTCTACTAGATACCAGGGTTTCATCTTTCGGTTTGGTC
  51    ATTTGGACCAGGGTGCCCGAAATATCGAAATTTCAGAAATTTCGGTTCGA
 101    AATTATATGAATTTTTGAACAAAATTTGATTAAATTAAACAAAATATTAT
 151    CAGATTTGCAAAAAATATGAAAAAAAAATCGGTCGAAATAATGTCGTATC
 201    TGGGTTCGATCCGAAATTTTGAACCCATGCTAGCTGCCAGGCTTTGGATT
 251    CTGAGCGTCACGTCAGGCACAATAAAATATTTGGGCCTCTAACTCTTCGT
 301    GGGCTGATCTGGGCCGTAGCAGACGAGAGAGCCCATGACACGATCTCATC
 351    AATTCCGTAGTGGCCACGGAACTCACGTAGCGCAAATGCCGCTCCCGTTT
 401    CCGCATCGTGCGATTTATCTCCTTTCTGTTTCCGAATTTTATTAGTAGTT
 451    GCGATATTATTAATACAGGTCTCGTAGCGGCCGCGTCTCCTCCTCCCTTA
 501    TATAAAGGCAGCGTTTCTGCAAGTTATTACCCAATCTACACGAGAGAG
                                                        BglII
 551    ATCGTTCGACGCATATAGAGAGAGAGAGAGATAGAGGCAAGATGCAGATC
                                                  M  Q  I
 601    TTCGTGAAGACGCTGACGGGGAAGACGATCACGCTGGAGGTGGAGAGCAG
         F  V  K  T  L  T  G  K  T  I  T  L  E  V  E  S  S
 651    CGACACCATCGACAACGTCAAGGCCAAGATCCAGGACAAGGAAGgtaata
         D  T  I  D  N  V  K  A  K  I  Q  D  K  E  G
 701    taacacgatatccctagcttcttcgtttgcatgttcatcttgtttaatcg
 751    ttgatgtcttgatgtcgtctcgcgatgatcgactgcacgtacgtacgccg
 801    tacatttgctggcattgctcgtcccgttaatttagtgactcatccttttt
 851    ttcgtacgtcgtgctcttgtgcgtctagacagtagaaatcatgtgttttg
 901    cactagatgcgtggtgggttgatactgccgaaattgttcaatattgtagt
 951    tgtagattagatcgatttgataaccaaaaaggaagccttgtacttttcca
1001    ttacattacataggtctaagcatgcgtgtgtttagtcgcagtaagcacgg
1051    agcaacaaatccaatctagccatctgcttatagttcgtcttcgctgtgta
1101    catgtttctattctgtcttagtagtttaaaacgatatgctagtaccgttt
1151    atctcttgatagggagtgccttcatcgatgacattgctgcataactgtaa
1201    ttaaagactcgttttcttcgttttcatggattaatatttacttccgagc
1251    ccattcgactagctaaaactcattcatatctctttcactgttgtatatat
1301    agGTATCCCTCCGGACCAGCAGCGCCTCATCTTCGCGGGGAAGCAGCTGG
            I  P  P  D  Q  Q  R  L  I  F  A  G  K  Q  L  E
1351    AGGATGGCCGCACCCTGGCCGACTACAACATCCAGAAGGAGTCGAC
         D  G  R  T  L  A  D  Y  N  I  Q  K  E  S
```

FIG. 4

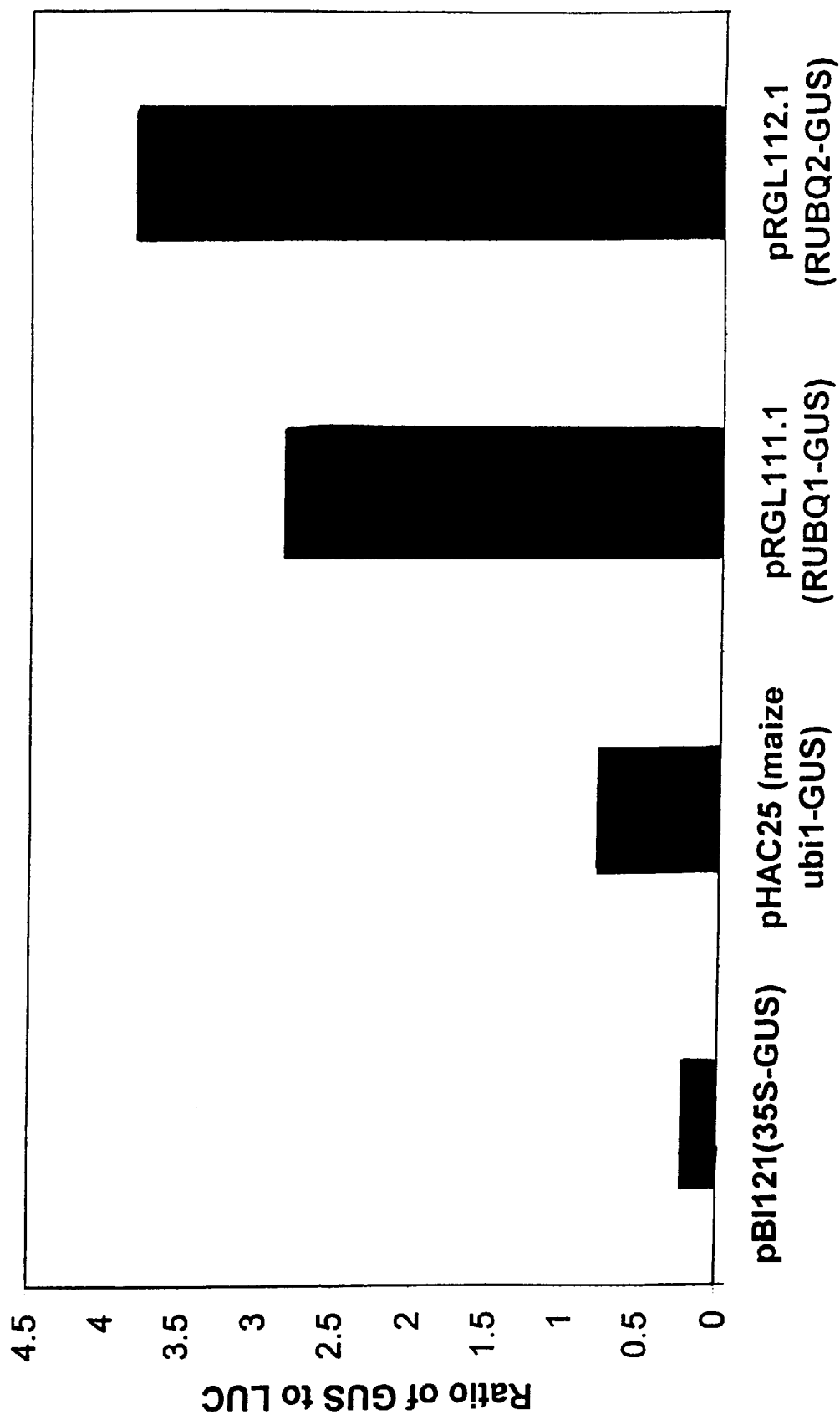
FIG. 5-A

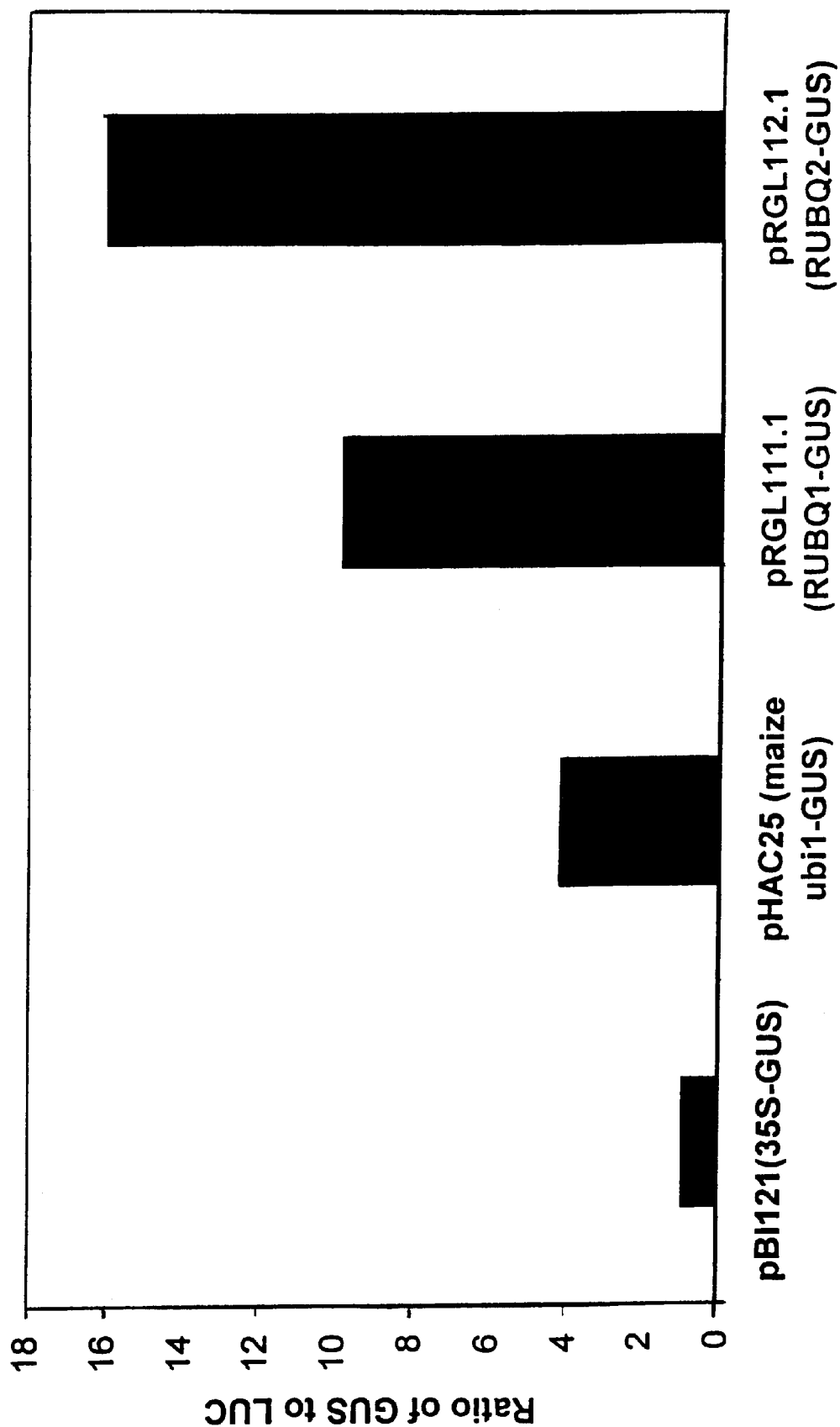
FIG. 5-B

RICE UBIQUITIN-DERIVED PROMOTERS

The benefit of the Mar. 2, 1999 filing date of provisional application 60/198,241 (which was a conversion of nonprovisional application 09/260,687), now abandoned, is claimed under 35 U.S.C. § 119(e).

This invention pertains to four novel ubiquitin promoters derived from ubiquitin genes isolated from rice (*Oryza sativa L.*), promoters that efficiently drive constitutive gene expression in transgenic plants.

Significant advances in cell biology and gene delivery techniques have allowed incorporation of foreign genes into many crop plants. Foreign genes are transferred into plants, named "transgenic plants," primarily to express proteins that will confer a beneficial trait, such as resistance to pathogenic micro-organisms or insects, resistance to herbicides, or tolerance to drought or other adverse environrments. Usually, the DNA coding region for the foreign gene is linked to a strong and constitutive DNA promoter region to ensure the efficient expression of the foreign gene in the transgenic cell.

A number of common promoters are used to drive foreign gene expression in transgenic plants. The cauliflower mosaic virus (CaMV) 35S promoter has been widely used in both dicots and monocots, but its effectiveness in monocots was found to be substantially less than in dicots. CaMV 35S was even inactive in certain cell types, such as pollen. See Guerrero et al., "Promoter sequences from a maize pollen-specific gene direct tissue-specific transcription in tobacco," Mol. Gen. Genet, vol. 224, pp. 161–168 (1990).

The maize alcohol dehydrogenase (Adh1) promoter has also been used in monocot transformation studies. This promoter has been shown to be 10 to 20 times more active than the CaMV 35S promoter in transformed rice protoplasts and cultured cells; however, the maize Adh1 promoter was not consitutively active in all transformed tissues. This promoter was induced by anaerobic stress in the transformed rice protoplasts. See Zhang et al., "Efficient regeneration of transgenic plants from rice protoplasts and correctly regulated expression of the foreign gene in the plants," Theor. App. Genet., vol. 76, pp. 835–840 (1988).

Promoters can be more effective if isolated from the same species as the transgenic plant. β-glucuronidase (GUS) expression under the control of a rice actin promoter (Act1) in transformed rice protoplasts was approximately 6-fold greater than expression under control of the maize Adh1 promoter. Activity of the rice actin promoter is dependent on the presence of an intact Act1 5' intron; i.e., removal of the intron resulted in no gene expression. See McElroy et al., "Isolation of an Efficient Actin Promoter for Use in Rice Transformation," The Plant Cell, vol. 2, pp. 163–171 (1990).

Ubiquitin is one of the most highly conserved proteins in eukaryotes. See Callis et al., "Ubiquitin and Ubiquitin Genes in Higher Plants," Oxford Surveys of Plant Molecular & Cell Biology, vol. 6, pp. 1–30 (1989). One physiological role for ubiquitin is to conjugate with a target protein as a recognition signal for protein degradation. See Viersta, R.D., "Proteolysis in plants: mechanisms and functions," Plant Molecular Biology, vol. 32, pp. 275–302 (1996). In higher organisms, ubiquitin has been shown to be encoded by two small gene families, named "polyubiquitin genes" and "ubiquitin fusion genes." Polyubiquitin genes comprise tandem head-to-tail repeats of 228 bp, with each repeat encoding 76 amino acids of a ubiquitin monomer. The number of tandem repeats reported varies between genes within genomes and between organisms, from 3 in Dictostylium to approximately 50 in *Trypanosoma cruzi*. On the other hand, the ubiquitin fusion gene family encodes a single repeat fused to one of two other polypeptides of either 52 or 76–80 amino acids. See Callis et al., "Ubiquitin and Ubiquitin Genes in Higher Plants," Oxford Surveys of Plant Molecular & Cell Biology, vol. 6, pp. 1–30 (1989). Studies of ubiquitin genes in a number of plants indicate that ubiquitin genes are expressed in all tissues; however, differential expression of the ubiquitin genes is also indicated among the ubiquitin gene family. Each tandem repeat or ubiquitin gene may be expressed differently over time and in different cells or tissues. Examples are given below.

The conditions that cause genetic expression of four ubiquitin-encoding cDNAs, including one ubiquitin fusion cDNA and three polyubiquitin cDNAs with 6 or 7 repeats, have been characterized in potato tuber. See Garbarino et al., "Expression of stress-responsive ubiquitin genes in potato tubers," Plant Molecular Biology, vol. 20, pp. 235–244 (1992). The ubiquitin fusion cDNA encoded a single ubiquitin unit fused to an 80 amino acid ribosomal extension protein. Expression of the ubiquitin fusion gene was induced by injury or ethylene, but not by heat. Expression of the three polyubiquitin genes differed: one was induced by injury, heat, or ethylene treatment; another was induced by injury or heat, but not by ethylene treatment; and the remaining gene was expressed at the highest level, but its expression decreased in response to injury, heat, or ethylene treatment.

Expression of the ubiquitin gene families may be dependent on the type and age of the plant tissue, as well as certain environmental factors. A polyubiquitin gene from *Nicotiana tabacum*, Ubi.U4, was expressed throughout the plant, except in just-fully-expanded leaves. See Genschik et al., "Sturcture and promoter activity of a stress and developmentally regulated polyubiquitin-encoding gene of *Nicotiana tabacum*," Gene, vol. 148, pp. 195B–202 (1994). In tomato, expression of a ubiquitin fusion gene, ubi3, was highest in young leaves and immature green fruits and lowest in mature leaves and petals; however, expression was reduced by heat or light deprivation. See Hoffman et al., "Isolation and characterization of tomato cDNA and genomic clones encoding the ubiquitin gene ubi3," Plant Molecular Biology, vol. 17, pp. 1189–1201 (1991). In parsley, expression of one polyubiquitin gene, ubi4, was predominant and was at comparable levels in all plant organs tested. See Kawalleck et al., "Polyubiquitin gene expression and structural properties of the ubi4-2 gene in *Petroselinum crispum*," Plant Molecular Biology, vol. 21, pp. 673–684 (1993).

Promoters from ubiquitin genes have been shown to drive reporter gene expression, usually GUS or chloramphenicol acetyl transferase (CAT), in transformed cells or plants. Such promoters have been isolated from Arabidopsis (Callis et al., "Ubiquitin Extension Proteins of *Arabidopsis thaliana*," The Journal of Biological Chemistry, vol. 265, no. 21, pp. 12486–12493 (1990)); sunflower (Binet et al., "Analysis of a sunflower polyubiquitin promoter by transient expression," Plant Science, vol. 79, pp. 87–94 (1991)); tobacco (Genschick et al., "Structure and promoter activity of a stress and developmentally regulated polyubiquitin-encoding gene of Nicotiana tabacum," Gene, vol. 148, pp. 195–202 (1994)); and maize (Christensen et al., "Maize polyubiguitin genes: structure, thermal perturbation of expression and transcript splicing, and promoter activity following transfer to protoplasts by electroporation," Plant Molecular Biology, vol. 18, pp. 675–689 (1992)).

The ubiquitin promoter ubi1 isolated from a maize polyubiquitin gene was shown to drive the expression of the CAT reporter gene more efficiently than the CaMV 35S promoter in maize protoplasts. See Christensen et al., "Maize polyubiguitin genes: structure, thermal perturbation of expression and transcript splicing, and promoter activity following transfer to protoplasts by electroporation," Plant Molecular Biology, vol. 18, pp. 675–689 (1992). The maize ubil-promoter has been used to express a herbicide resistance gene in rice. See Toki et al., "Expression of a Maize Ubiquitin Gene Promoter-bar Chimeric Gene in Transgenic Rice Plants," Plant Physiol, vol. 100, pp. 1503–1507 (1992).

U.S. Pat. Nos. 5,614,399 and 5,510,474 describe a promoter from a maize polyubiquitin gene. The promoter regulates expression of a maize polyubiquitin gene containing 7 tandem repeats. Expression of this maize ubiquitin gene was constitutive at 25° C., and was induced by heat shock at 42° C. The promoter was successfully tranformed and expressed in other monocot plants in addition to maize, including wheat, barley, and rice. See Christensen et al., "Ubiquitin promoter-based vectors for high-level expression of selectable and/or screenable marker genes in monocotyledonous plants," Transgenic Research, vol. 5, pp. 213–218 (1996). In contrast, expression of this maize promoter in idicot plants was relative low. For example, the CAT reporter gene expression under control of a maize ubiquitin promoter was 10 times less than that under control of the CaMV 35S in tobacco protoplasts. See Christensen et al., Plant Mol. Biol., vol. 18, pp. 675–689 (1992). In the maize ubil promoter region, a TATA box was found at position of –30, and two overlapping heat shock sequences, 5'-CTGGTCCCCTCCGA-3' (SEQ ID NO 13) and CTCGAGATTCCGCT-3'(SEQ ID NO 14), were found at positions –214 and –204. The canonical CCAAT and the GC boxes were not found in the promoter region, but the sequence 5-CACGGCA-3' (function unknown) occurred four times, at positions –236, –122, –96, and –91 of the promoter region. See Christensen et al., "Maize polyubiguitin genes: structure, thermal perturbation of expression and transcript splicing, and promoter activity following transfer to protoplasts by electroporation," Plant Molecular Biology, vol. 18, pp. 675–689 (1992).

U.S. Pat. No. 5,773,705 describes a method to use ubiquitin monomers to enhance gene expression. The polyubiquitin gene was translated as the precursor polyubiquitin protein. The precursor polyubiquitin protein was then split into a 76 amino-acid ubiquitin monomer. If a single repeat of the ubiquitin DNA sequence was added upstream of a structural gene, a fusion protein was produced. The ubiquitin monomer was then cleaved from the fusion protein to release the protein encoded by structural genes. This method to enhance gene expression was documented for several polyubiquitin genes.

U.S. Pat. No. 5,723,757 describes a method to increase a tissue-specific (the storage or sink organ) expression of a desired DNA sequence by linking the DNA sequence to either a class I patatin promoter or a B33 promoter.

U.S. Pat. No. 5,723,765 describes a method of creating a transgenic plant that contains a gene whose expression can be controlled by application of an external stimulus. U.S. Pat. No. 5,750,866 describes a maize AHAS promoter used for heterologous gene expression in plants.

Rice is one of most important crops in the world, and is a model plant for genetic engineering. Strong promoters isolated from the rice genome will facilitate genetic improvement of rice. Additionally, such promoters may be effective in other plants, monocots and dicots.

We have sequenced four rice ubiquitin genes, including the promoter region for each. Of the four genes, two belong to the family of polyubiquitin genes, designated RUBQ1 and RUBQ2; and the other two belong to the ubiquitin fusion gene family, designated RUBQ3 and RUBQ4. The two polyubiquitin genes both comprise 6 ubiquitin-monomers in the coding region. Expression of the polyubiquitin gene, RUBQ2, was high in all rice plant tissues that were tested. Expression of the RUBQ2 gene was also induced by heat-shock treatment. Promoters isolated from RUBQ1 and RUBQ2 genes were shown to drive strong and constitutive expression of foreign genes in transformed rice plants.

The two promoters from the polyubiquitin genes were much more effective than the maize ubiquitin promoter in gene expression in rice. GUS expression under control of either RUBQ1 or RUBQ2 promoter was much higher than that under control of the CaMV 35S or maize ubiquitin promoter. Additionally, transgenic rice plants stably expressing the GUS gene under control of the RUBQ1 or RUBQ2 promoter have been developed. Strong GUS expression in roots was observed. However, GUS expression in roots of transgenic plants derived from transformation with CaMV 35S promoter-GUS construct was not readily detectable.

BRIEF DESCRIPTION OF THE DRAWINGS

FIG. 1 documents the 3184 base DNA sequence of rice polyubiquitin gene RUBQ1 and its deduced amino acid sequence. The TATAAATA box at position 811 is underlined. The intron immediate upstream of the coding region extends from positions 920 to 1701; and the ubiquitin coding region extends from positions 1702 to 3072, followed by a 3'- untranslated region.

FIG. 2 documents the 4442 base DNA sequence of rice polyubiquitin gene RUBQ2 and its deduced amino acid sequence. The ATAAATA box at position 1712 is underlined. The intron immediate upstream of the coding region extends from positions 1824 to 2785; and the ubiquitin coding region extends from positions 2786 to 4159, followed by a 3'- untranslated region.

FIG. 3 shows the 1846 base DNA sequence of rice ubiquitin fusion gene RUBQ3 and its deduced amino acid sequence. The putative TATATAA box at position 275 is underlined. The single repeat of the ubiquitin-encoding region extends from positions 383 to 1276, including a single putative 665 base pair intron within the repeat.

FIG. 4 shows the 1396 base DNA partial sequence of rice ubiquitin fusion gene RUBQ4 and its deduced amino acid sequence. The putative TTATATAAA box at position 498 is underlined. The coding region for a single ubiquitin repeat extends from positions 592 to 1394, including a single putative 608 base pair intron within the repeat.

FIG. 5A illustrates β-glucuronidase activity from transient assays of rice suspension cells after transformation with pRGL111 (RUBQ1-promoter-GUS), pRGL112 (RUBQ2-promoter-GUS), pRGL131 (CaMV 35 S-GUS), or pHAC25 (maize ubil-promoter-GUS) from one experiment.

FIG. 5B illustrates β-glucuronidase activity from transient assays of rice suspension cells after transformation with pRGLIII (RUBQ1-promoter-GUS), pRGL112 (RUBQ2-promoter-GUS), pRGL131 (CaMV 35 S-GUS), or pHAC25 (maize ubil-promoter-GUS) from a second experiment.

DEFINITIONS

"CAAT box" is part of a conserved sequence located upstream of the start point of eukaryotic transcriptional units. This sequence may be involved in binding transcriptional factors such as RNA polymerase II.

"CAP site" is the position of linking the 5' end of a guanine nucleotide to the terminal base of a mRNA molecule. The cap site usually occurs at the site of transcription initiation.

A "chimeric gene" is a gene comprising a promoter and a structural gene from different sources.

A "consensus sequence" is an artificial sequence in which the base in each position represents the base most frequently found in comparing actual sequences from different alleles, genes, or organisms.

"Expression" is the transcription or translation of a structural gene.

"GC box" is a common promoter element that is believed to increase promoter activity.

A "heterologous gene" is a gene combining complementary strands derived from different homologous DNA molecules.

"A promoter" is that portion of the DNA upstream from the coding region that contains the binding site for RNA polymerase II to initiate transcription of the DNA.

A "reporter gene" is a coding unit whose product is easily assayed, e.g., CAT and GUS genes. Expression of a reporter gene can be used to assay function of a promoter connected to the reporter gene.

"TATA box" is an element in the promoter, located approximately 30 bases upstream of the transcription start site. The TATA box is associated with general transcriptional factors including RNA polymerase II.

The present invention relates to promoters from rice ubiquitin genes and the use of those promoters to drive gene expression in transformed plants. Four promoters from rice ubiquitin genes have been sequenced and cloned. Two polyubiquitin genes, RUBQ1 (SEQ ID NO 1) and RUBQ2 (SEQ ID NO 3), and two ubiquitin-fusion genes, RUBQ3 (SEQ ID NO 5) and RUBQ4 (SEQ ID NO 8), from rice have been characterized. Both polyubiquitin genes, RUBQ1 and RUBQ2, contain six ubiquitin monomers in the coding region with an intron immediately upstream of the coding region. (FIGS. 1 and 2) The two ubiquitin-fusion genes, RUBQ3 (SEQ ID NO 5) and RUBQ4 (SEQ ID NO 9), contain a single ubiquitin monomer with one putative intron within the ubiquitin monomer-coding region. (FIGS. 3 and 4). The polyubiquitin gene, RUBQ2, is expressed at high levels in all rice tissues tested.

The two rice polyubiquitin promoters isolated from RUBQ1 and RUBQ2 have been used to drive GUS gene expression in rice. Chimeric RUBQ1-promoter/GUS and RUBQ2-promoter/GUS genes were introduced into rice cultured cells via particle bombardment. For comparison, the rice cultured cells were also transformed with a vector carrying a chimeric maize ubi1-promoter/GUS or CaMV35S/GUS promoter-gene combination. GUS expression under control of either RUBQ1 or RUBQ2 promoter was much higher than that under control of the CaMV 35S or maize ubiquitin promoter.

Transgenic rice plants stably expressing the GUS gene under control of the RUBQ1 or RUBQ2 promoter have been developed. Strong GUS expression in roots was observed. However, GUS expression in roots of transgenic plants derived from transformation with CaMV 35S promoter-GUS construct was not readily detectable.

The rice ubiquitin promoter can be used in combination with any structural gene to make a chimeric gene; the chimeric gene can then be inserted into a cloning vector, which can self-replicate in prokaryotic host cells to produce large quantities of the molecules for plant transformation. Many different methods have been developed to introduce foreign DNA into plant cells, including particle bombardment, electroporation, protoplast transformation and *Agrobacterium tumefaciens*-mediated transformation.

The rice ubiquitin promoters can be used to regulate a variety of structural genes, and will cause high constitutive expression of the structural gene in transgenic plants. The chimeric genes are introduced into plant tissue in such a manner that the promoter/structural gene combination is efficiently expressed. We have demonstrated a high level of GUS expression under the control of promoters from both polyubiquitin genes in rice cultured cells, as well as in transgenic rice plants. It is expected that the rice ubiquitin promoters can be combined with any structural gene for efficient constitutive expression in transgenic plants. It is also contemplated that the rice ubiquitin promoters of this invention are generally applicable to the efficient expression of structural genes in other monocotyledonous plants in addition to rice, as well as in dicotyledonous plants.

The rice polyubiquitin gene RUBQ2 was abundantly expressed in all the rice tissues tested, including roots, seedlings, old leaves, just-fully-developed leaves, young leaves, and panicles. Promoters from the two polyubiquitin genes, RUBQ1 and RUBQ2, have been demonstrated to drive GUS expression very efficiently in transformed rice cells and in transgenic plants. The promoters can thus be used to express a variety of structural genes in different plants, including genes for herbicide resistance, resistance to plant pathogens, and tolerance to drought or other adverse environmental conditions.

EXAMPLE 1

Isolation and Characterization of Ubiquitin Genes from Rice

A. DNA Isolation and Southern Analysis

DNA from seedlings of each of three rice varieties, Cypress, Jackson and Gulfinont (LSU Agricultural Center, Baton Rouge, La.), was isolated using the CTAB method as described by Dellaporta et al., Plant Mol. Biol. Report, vol. 1(4), p. 19 (1983). The DNA from each was completely digested with the restriction enzymes Hind III, XbaI, and EcoR I. The digests were then fractionated in an 0.8% agarose gel and transferred onto a nylon membrane (Boehringer Mannheim Biochemicals, Indianapolis, Ind.), according to procedure described in the molecular cloning manual (Sambrook et al., Molecular Cloning: A Laboratory Manual, 2d Edition, CSH Laboratory Press, pp. 13.11–13.17 (1987)). 1989). The membrane was pretreated for 6 hours at 65° C. in 5×Denhardts solution, 100 ug/ml denatured sperm DNA, 6×SSC, and 0.5% SDS. Sugarcane ubiquitin cDNA (from the USDA, Hawaii Agriculture Research Center) was $^{32}$P-labeled using random primer labeling kit purchased from Boehringer Mannheim Biochemicals (Indianapolis, Indiana). Hybridizations were performed overnight at 65° C. in the same prehybridization solution by adding the $^{32}$P-labeled probe. The membrane was then washed in 2×SSC, 0.1% SDS at 65° C. for 15 min, followed by a second rinse in 0.2×SSC, 0.1% SDS solution at 65° C. for another 15 min. Autoradiography was carried out at −80° C. with Kodak MS X-ray film and one intensifying screen. Four or five fragments strongly hybridized to the sugarcane ubiquitin cDNA probe.

B. Isolation of Genonic Clones

A rice genomic library (bacterial artificial chromosomes, BAC) comprising 11,000 clones with an average DNA insert size of 125 Kb was provided by the University of California, Davis, Calif. The sugarcane cDNA clone Scubi 561 (USDA, Hawaii Agriculture Research Center) was used as a probe to screen the BAC library. Twenty-three clones showed hybridization signals when probed by $^{32}$P-labeled sugarcane cDNA. Seven clones showing the strongest hybridization signals were chosen for further characterization.

The seven clones were completely digested with Hind III enzyme, and the fragments were then separated on a 0.7% agarose gel. The DNA was transferred onto a nylon filter and hybridized with $^{32}$P-labeled sugarcane ubiquitin cDNA. Four Hind III fragments of different lengths showed hybridization signals: a 14 kb fragment from clone 02 and clone 03; an 8.3 kb fragment from clone 15 and 24; and two fragments of 7.8 kb and 4.8 kb from clone 01. These four fragments were purified from agarose gels and cloned into the HindIII site of the Bluescript SK vector (Stratagene, LaJolla, Calif.). The resultant clones, pRGL104.1, pRGL105.1, pRGL106.1 and pRGL107.1, carried 7.8 kb (clone 01), 4.8kb (clone 01), 14kb (clone 02 or 03) and 8.3 kb (clone 15 or 24) DNA fragments, respectively.

C. Restriction Mapping, Subcloning, and Sequencing of the Four Rice Ubiquitin Genes All restriction enzymes and modifying enzymes were purchased from New England Biolab (Beverly, Mass.) and GIBCO (Gaithersbury, Md.). Detailed restriction maps for the above 4 fragments were made. The ubiquitin gene position on the fragment was estimated based on the enzyme digestion followed by Southern Blotting. A set of overlapping fragments within the ubiquitin gene and the nearby region were subcloned into Bluescript SK (Stratagene, LaJolla, Calif.) for DNA sequencing. High quality, double-stranded DNA for sequencing was obtained using a plasmid mini-preparation kit (Qiagen, Santa Clara, Calif.). DNA sequencing was performed on an ALF-WIN Automatic DNA sequencer (Pharmacia, Piscataway, N.J.) using a thermal cycle sequencing kit from Pharmacia according to the manufacturer's recommendation. Both strands of the plasmid inserts were sequenced using Cy-5 labeled universal primers M13 and M40. For plasmids having longer inserts, new primers were synthesized based on sequencing data and Cy-5 labeled by Pharmacia. The Primer-based sequencing strategy was used to determine DNA sequences of the four ubiquitin genes isolated from the rice genomic library by the procedure described in Sambrook et al., Molecular Cloning: A Laboratory Manual, 2d Edition, CSH Laboratory Press, pp. 13.11–13.17 (1987).

Sequence analysis indicated that each of the four fragments contained a different rice ubiquitin gene. The genes isolated from clone pRGL106.1, clone pRGL107.1, clone pRGL104.1 and pRGL105.1 were designated RUBQ1, RUBQ2, RUBQ3 and RUBQ4, respectively. RUBQ1 and RUBQ2 were polyubiquitin genes with six repeats of ubiquitin monomers in the coding region. RUBQ3 and RUBQ4 were ubiquitin fusion genes. They were physically linked because they were derived from the same BAC clone (designated clone 01).

The 3184 base DNA sequence of the polyubiquitin gene RUBQ1 is shown in FIG. 1 (SEQ ID NO 1). The ubiquitin-coding region is from positions 1702 to 3072. Immediately upstream of this coding region is a 782 base intron extending from positions 920 to 1701. A 1.7 kb RUBQ1-promoter can be isolated as a 2kb SalI and XhoI restriction fragment of RUBQ1. The 782 bp intron and a 48 bp ubiquitin-coding region are included in this promoter. Because part of the coding region is in the promoter, insertion of a structural gene downstream of the promoter will result in a fusion protein, comprised of the amino acids produced by the 48 bp ubiquitincoding region and those produced by the structural gene of choice. A TATA box is located at position 811, approximately 30 bases upstream of the putative CAP site. A GC box is found at position 657 (154 bases upstream from the TATA box); and a CAAT box is found at position 399 (413 bases upstream from the TATA box). Two separate heat shock sequences, 5'-CTCGATATCTCCGCG-3' (SEQ ID NO 15) and 5'-CTGGACCCGCCCCCT-3' (SEQ ID NO 16), are found at positions 630 and 652, respectively. These sequences show 47% homology with the Drosophila heat shock consensus sequence 5'-CTGGAATNTTCTAGA-3' (SEQ ID NO 17). See U.S. Pat. No. 5,614,399.

The 4442 base DNA sequence of the other polyubiquitin gene, RUBQ2, is shown in FIG. 2 (SEQ ID NO 3). The ubiquitin-coding region is found from positions 2786 to 4159. A 926 base intron is located immediately upstream of the coding region, extending from positions 1824 to 2785. A 2.8 kb RUBQ2-promoter can be isolated as a PstI and XhoI restriction fragment from RUBQ2. This promoter contains the 962 base intron followed by a 48 base ubiquitin-coding region. Again, a fusion protein is produced when a structural gene is inserted downstream of this RUBQ2-promoter with the 48 base ubiquitin-coding region. A TATA box is found at position 1712, approximately 30 bases upstream of the putative cap site. Within the promoter region, a GC box is found at position 1454 (259 bases upstream of the TATA box). One interesting feature of this promoter is an enhancer_core consensus sequence beginning at position 1019 (694 bases upstream of the TATA box). This enhancer_core consensus sequence 5'GGTGTGGAAA(or TTT)G-3' (SEQ ID NO 18) has been found in both animal and plant genes and is believed to function as a global enhancement element for gene expression (Khoury et al., Enhancer Elements. Cell, vol. 33, pp. 313–314 (1983)). Additionally, a single heat shock consensus sequence is found beginning at position 1536 (176 bases upstream of the TATA box).

The 1846 base DNA sequence of one rice ubiquitin fusion gene is shown in FIG. 3 (SEQ ID NO 5). A single repeat of the ubiquitin-coding region extends from positions 383 to 1276 and is interrupted by an intron element from positions 488 to 1153. A 392 base promoter of RUBQ3 can be isolated as a Hind III/Bgl II restriction fragment. A TATA box is found beginning at position 275. However, no CAAT box, GC box, or heat shock sequence is found in this promoter region.

The 1396 base DNA sequence of RUBQ4 is shown in FIG. 4 (SEQ ID NO 9). A single repeat of the ubiquitin-coding region extends from positions 592 to 1394. This coding region is interrupted by a putative intron from positions 697 to 1304. The 600 base promoter of RUBQ4 can be isolated as a Hind III/ Bgl II restriction fragment. A TATA box is found at position 498. Similar to the other ubiquitin fusion gene RUBQ3, the RUBQ4 gene does not carry a GC box, CAAT box, or heat-shock consensus sequence in the promoter region.

Both rice polyubiquitin genes RUBQ1 and RUBQ2 encode 6 repeats of the ubiquitin monomer. The last repeat contains a glutamine amino acid extension. DNA sequences in the coding region between these two rice polyubiquitin genes show 87% homology. The deduced amino acid sequence of the two rice ubiquitin genes is identical. See FIG. 1 and FIG. 2; SEQ ID NO 2 and SEQ ID NO 4. The deduced amino acid sequences of the ubiquitin monomer of the two rice ubiquitin fusion gene RUBQ3 and RUBQ4 are also identical to that encoded by rice polyubiquitin genes, except that the RUBQ4 sequence is not complete. See SEQ ID NO 6 and SEQ ID NO 10. Though the sequence of the coding region is highly conserved, considerable variation occurs in the promoter region including the intron.

Compared to the maize ubiquitin gene, which contains 7 repeats in the coding region, the two rice polyubiquitin genes contain only 6 repeats in the coding region. Though the coding region is conserved among ubiquitin genes, showing 88% homology between maize (Christensen et al., Maize polyubiguitin genes: structure, thermal perturbation of expression and transcript splicing, and promoter activity following transfer to protoplasts by electroporation. Plant Molecular Biology, vol. 18, pp. 675–689 (1992)) and the two rice polyubiquitin genes described here, their promoter and intron regions vary considerably. Computer-assisted analysis showed that the maximum matching percentage of the intron between the maize and the two rice polyubiquitin genes is 53% and 50%, respectively. The maximum matching percentage of promoter sequence between maize and the two rice polyubiquitin genes is 55% and 52%, respectively. The sequence 5-CACGGCA-3', which occurs four times at −236, −122, −96, −91 of the maize promoter region, does not occur in any of the rice ubiquitin promoters. Two commnon promoter elements, the CAAT box and GC boxes, which play a major role in determining the efficiency of the promoter, are found in the rice polyubiquitin promoters, but are absent in the maize ubiquitin promoter. In addition, activity of the rice polyubiquitin promoters linked to a reporter gene was at least three times that of the maize ubiquitin promoter when transferred by particle bombardment into cultured rice cells.

Differences between maize and rice ubiquitin genes can also be seen in the restriction map of the ubiquitin genes. For example, the Pst I site at the intron/exon junction in the maize polyubiquitin gene is not found in rice ubiquitin genes. The BglII site found in the leading sequence of the maize ubiquitin gene is not shown in a corresponding region of rice ubiquitin genes.

The heat shock sequence similar to Drosophila heat shock consensus element 5'-CTGGAATNTTCTAGA-3' (SEQ ID NO 15) is found once at position 1536 (176 bases upstream from the TATA box) in the RUBQ2-promoter. In the RUBQ1-promoter, two separate heat shock sequences are found at position 630 (182 bases away from the TATA box) and position 652 (160 upstream of the TATA box), both of which show 47% homology with the Drosophila heat shock sequence. No heat shock sequence is found in promoter regions of the ubiquitin fusion genes RUBQ3 and RUBQ4. In comparison with the single heat shock consensus sequence found in the rice ubiquitin promoter region, the maize ubi1-promoter contains two overlapping heat shock sequences at positions −214 and −204. Similar overlapping heat shock sequences have also been reported for a chicken ubiquitin gene promoter (Bond et al., Ubiquitin Is a Heat Shock Protein in Chicken Embryo Fibroblasts. Molecular and Cellular Biology, vol. 5, no. 5, pp. 949–956).

It should be also noted that a shortened promoter that will still retain promoter activity can be obtained using restriction sites within the promoter. In particular, the 48 base coding region could be removed from both promoters of RUBQ1 and RUBQ2 by exonuclease digestion. If such a shortened promoter were then combined with a structural gene, the translation of the structural gene would begin at the start site of the structural gene itself.

EXAMPLE 2

Constructs Containing Chimeric RUBQ1/GUS, RUBQ2/GUS and RUBQ2/LUC Genes

Promoter Isolation and Chimeric Gene Construction

A Hind III/EcoR I fragment containing a GUS coding region and a NOS poly(A) addition site was removed from pBI 101 (Clonetech, Palo Alto, Calif.) and inserted into pUC 18, generating the plasmid pRGL110. The promoter to be tested was inserted into the polylinker upstream of the GUS gene. The plasmid pRGL110 contains a Sal site 27 bases upstream of the GUS ATG. This SalI site of pRGL110 is in the same frame as an XhoI site at +42 (relative to the ATG) in the ubiquitin-coding region of both RUBQ1 and RUBQ2. For expression of the GUS gene under control of the rice polyubiquitin promoters, the 1.7 kb SalI/XhoI fragment from the polyubiquitin gene RUBQ1 and the 2.8 kb PstI/XhoI fragment from RUBQ2 were ligated into pRGL1 10, creating the plasmids pRGL111-1 (RUBQ1-GUS-NOS) and pRGL112-1 (RUBQ2-GUS-NOS). It is believed that the intron region, or a portion thereof, of each of the above rice promoter regions plays an important role in enhancing expression levels in transgenic cells or plants.

A chimeric gene containing the RUBQ2 promoter linked to a luciferase (LUC) coding region was constructed as follows: vector pGL103 carrying the structural gene for LUC and an SV40 polyA addition site was purchased from Promaega Corporation (Madison, Wis.). The SV40 polyA addition site in pGL103 was replaced with a NOS polyA addition site and a 300 bp XbaI/BglII fragment from pDM302, creating a modified plasmid, pRG103. The RUBQ2 promoter, a HindIII/BamH I fragment, was removed from vector pRGL112-1, blunt-ended by treating with T4 DNA polymerase (New England Biolab, Beverly, Mass.), and ligated into the blunt-ended Hind III site of the modified pRGL103. The resultant construct was termed pRUBQ2-LUC, with the luciferase expression under control of the RUBQ2-promoter.

Two control plasmids were used for transient transformation: pAHC 25, containing maize ubi 1 promoter-GUS cassette; and pBI121, containing 35S promoter-GUS cassette.

EXAMPLE 3

Transferring and Expression of the Recombinant DNA in Cultured Rice Cells

Cultured rice cells were derived from mature seeds of the rice public variety Taipei 309. The dehulled mature seeds were sterilized and cultured on 0.8% agarose MS media (Sigma Chemical Co., St. Louis, Mo.) containing 4 ppm 2,4-D for three weeks. The cultured cells were then transferred into R2 liquid media containing 4 ppm 2,4-D as a suspension culture. The R2 media was changed once a week. These cultured rice cells were used for particle bombardment 4 months after initiation of the liquid suspension culture.

Approximately 200 mg fresh cultured rice cells were evenly distributed over the surface of a piece of filter paper (approximately 7 cm diameter) centered on a 7.5 cm petri dish. The DNA to be transferred was isolated using a Qiagen plasmid kit. The amount of DNA used for bombardment was adjusted to have the same molar amounts for each of the constructs. Each of the four plasmids (pRGL111, pRGL112, pAHC25 and pBI121) was co-transferred into the rice cultured cells with the plasmid RUBQ2-LUC-NOS by particle bombardment. Luciferase activity was used as an internal control to adjust for GUS expression under control of the different promoters, according to the procedure described by Norris et al., Plant Mol. Biol., vol. 21, pp. 895–906 (1993).

Two constructs with equal molar amounts (equivalent to 5 μg DNA for pRUBQ2-LUC) were precipitated onto gold particles (0.1 μm in diameter) and introduced into cells according to the procedure as described in Christou et al., Bio/Technology, vol. 9, pp. 957–962 (1991). Following bombardment, the cells were incubated for 2 days at 25° C. Cell extracts for both GUS and luciferase (LUC) assay were prepared according to the following procedure. The bombarded cells were transferred into a 50 ml tube containing 300 μl 1×reporter assay buffer (Promeaga, Madison, Wis.) and homogenized for 2 min. Then the extracts were centrifuged twice at 10,000 g for 5 min at 4° C. The final supernatant was transferred into a clean tube and stored at −80° C. until assayed for GUS and LUC activity. Twenty microliters of thawed supernatant were used to measure GUS activity in a TKO 100 fluorimeter (Hoefer Co. Madison, Wis.), according to the method described by Jefferson et al., EMBO J., vol. 6, pp. 3901–3907 (1987). GUS activity was expressed as a change in fluorescence units per minute, where a change of 100 fluorescent units corresponded to 3 pmol of methyl umbelliferone (MU) produced.

For the luciferase assay, 20 μl of thawed supernatant were assayed in a scintillation analyzer using a luciferase assay kit (Promega, Madison, Wis.). Measurements were taken 1.5 min after mixing the supernatant with the luciferase assay reagent. The LUC activity was expressed as counts per minute (CPM). The assay was standardized with purified recombinant luciferase such that 1 light unit (L.U.) was equivalent to $2.8 \times 10^5$ CPM.

Two separate experiments were conducted, each with four replicates of each construct. The activity of each promoter driving GUS expression was expressed as the ratio of GUS activity (pmol/min) to LUC activity (L.U.). The results are shown in FIG. 5-A and FIG. 5-B for the two independent experiments. GUS expression under the control of the RUBQ1 promoter was ten times greater than GUS expression under the control of CAMV 35S promoter, and three times greater than expression under the control of the maize ubiquitin promoter. GUS expression under the control of the RUBQ2 promoter was 15 times greater than when under the control of CaMV 35S promoter and three times greater than when under the control of the maize ubiquitin promoter. Thus, the rice ubiquitin promoters were substantially more effective than either the CaMV 35S promoter or the maize ubiquitin promoter.

EXAMPLE 4
Transgenic Rice Plants Expressing the GUS Gene Under the Control of the Rice Ubiquitin Promoter A 7 kb Hind III fragment containing a hygromycin-resistance gene was removed from the common construct pTRA151 and ligated into the HindIII site of each of the following three plasmids: pRGL111-1 (RUBQ1-GUS), pRGL112-1 (RUBQ2-GUS), and pRGL115 (CaMV 35S-GUS). The resulting plasmids were designated pRGL 117, pRGL 118, and pRGL 131, respectively. Each of the plasmids was transferred into rice suspension cells as described above in Example 3. The transformed rice cells were then selected on solid MS media containing 4 ppm 2,4-D and 50 ppm hygromycin. After a one-month incubation at room temperature, the growth of resistant cultured cells was seen. The resistant cells were transferred to MS regeneration media containing 2 ppm kinetin, 0.1 ppm naphthalene acetic acid (NAA), and 50 ppm hygromycin. After about 4 weeks of culture, hygromycin-resistant rice plants were generated. These plants were transferred into MS rooting media without any hormones for two weeks and were then transferred to the greenhouse. GUS expression in the hygromycin-resistant transgenic cells was monitored by adding the GUS substrate 5-bromo-4-chloro-3-indolyl-beta-D-glucuronide (X-Glu) according to the method described by Jefferson et al., EMBO J., vol. 6, pp. 3901–3907 (1987). Resistant cells transformed with a plasmid that contained either of the two rice polyubiquitin promoters and a GUS cassette (plasmids pRGL117 and pRGL118) turned blue immediately after the substrate X-Glu was added. In contrast, a blue precipitate formed much more slowly (after more than three days) in the resistant cells transformed with the CaMV 35S promoter and GUS cassette (plasmid pRGL131). These results demonstrated that the two rice polyubiquitin promoters drove gene expression much more efficiently than the CaMV 35S promoter in transgenic rice plants.

Additionally, ten independent hygromycin-resistant calli were randomly selected from lines grown for two months (approximately twenty generations) to determine whether the calli were stably transformed. These calli were assayed for GUS expression, using the assay as described in Example 3. The results are shown in Table 1. The GUS activity from constructs containing RUBQ1 and RUBQ2 promoters in stably transformed calli was 22 to 48 fold greater than those containing the CaMV 35S promoter.

TABLE 1

Comparison of GUS expression from constructs made from rice ubiquitin promoters and CaMV 35 S promoter in stably transformed calli

| Construct | No. of Calli | GUS Activity* | Fold |
| --- | --- | --- | --- |
| Control | 5 | 1.17 ± 0.23 | |
| pRGL131 (35S-GUS) | 10 | 20.73 ± 10.84 | 1 |
| pRGL117 (RUBQ1-GUS) | 10 | 458.32 ± 252.80 | 22 |
| pRGL118 (RUBQ2-GUS) | 10 | 996.53 ± 593.33 | 48 |

*GUS activity as MU pmol/mg-fresh cells/min.
P-values indicated statistically significant differences among the three constructs.

To test for expression in older rice plants, transgenic rice plants (first generation, $T_0$) containing chimeric rice ubiquitin promoter or CaMV 35S promoter-GUS genes were generated and grown from calli as described above. About 15 independent transgenic rice plants were selected for GUS activity assay. Leaves at the tillering and heading stages of the transgenic rice were harvested and homogenized in liquid nitrogen. About 50 mg fresh leaves from each transgenic rice plant were assayed for the GUS expression. The results are shown in Table 2. At the heading stage, the GUS activity from constructs containing RUBQ1 and RUBQ2 promoters in transgenic rice plants was 8 to 35 times greater than the construct containing the CaMV 35S promoter.

TABLE 2

Comparison of GUS expression from constructs made from rice ubiquitin promoters and CaMV 35S promoter in transgenic rice plants

| Construct | No. of Plants | Tillering Stage | | Heading Stage | |
|---|---|---|---|---|---|
| | | GUS Activity* | Fold | GUS Activity* | Fold |
| Control | 5 | 1.18 ± 0.31 | | 1.37 ± 0.26 | |
| pRGL131 (35S-GUS) | 11 | 20.07 ± 9.22 | 1 | 21.56 ± 11.08 | 1 |
| pRGL127 (RUBQ1-GUS) | 17 | 229.19 ± 198.47 | 11 | 169.99 ± 131.59 | 8 |
| pRGL128 (RUBQ2-GUS) | 13 | 555.40 ± 428.40 | 28 | 755.70 ± 638.46 | 35 |

*GUS activity as Mu pmol/mg-fresh leaf/min.
P-values indicated statistically significant differences among the three constructs.

EXAMPLE 5
Rice Ubiquitin Gene Expression

The rice variety Cypress was grown in the greenhouse as a source for different tissues, including roots, seedlings, old leaves, just-fully-developed leaves, young leaves, and young panicles. To test the response of the rice ubiquitin genes to heat shock treatment, 2-week-old-seedlings were immersed in 42° C. water for 20 min. After this heat shock treatment, RNA was isolated from the seedlings at 0 min. 30 min, 60 min, and 120 min, according to standard protocols (Swnbrook et al., 1989). Twenty micrograms of RNA were separated on a 1% agarose gel containing formaldehyde. The RNA was then extracted from the gel and transferred onto a nylon membrane. The 350 bp XhoI fragment of the ubiquitin-coding region from polyubiquitin gene RUBQ2 was labeled with $^{32}$P using a random-primer labeling kit. (Promega, Madison, Wis.) Prehybridization, hybridization, and washing conditions were conducted according to the procedure described in Sambrook et al., 1989. Autoradiography was done by overnight exposure to Kodak MS X-ray film.

The results indicated that the rice polyubiquitin gene RUBQ2 is abundantly expressed in all tissues tested. Additionally, expression of RUBQ2 was elevated by heat-shock treatment, which is consistent with the heat shock sequence found in this promoter.

Rice is a monocot, and promoters isolated from one monocot plant gene generally function in other monocot plants. For illustration, the rice Act1 promoter has been used to drive gene expression in maize protoplasts, and the maize ubiquitin ubi promoter has been used to express genes in wheat, barley, oat, and rice (Christensen et al., (1996) Transgenic Research 5:213–218). The rice ubiquitin promoters described here can be used to drive gene expression in other monocot plants in addition to rice, including wheat, oat, rye, millet, maize and sorghum etc. They may also prove effective in dicot plants.

The rice ubiquitin promoters may be linked to structural genes including but not limited to those for herbicide resistance, resistance to pests, and tolerance to drought or other adverse environmental conditions.

EXAMPLE 6
Fusion of Rice Ubiquitin Promoters with a Herbicide-resistant Coding Sequence The promoter isolated from RUBQ2 will be fused to a gene known to convey herbicide-resistance, for example, the phosphinothrycin acetyl transferase (PAT gene) (AgrEvo USA Company, Wilmington, Del.), which confers resistance to the herbicide LIBERTY™. A plasmid containing the chimeric gene (the RUBQ2 promoter and the PAT coding sequence) will made according to the procedure in Example 2. This plasmid will be transferred by particle bombardment into rice cells from which transgenic rice plants will be grown as in Examples 3 and 4. The trangenic rice plants will then be grown and evaluated for resistance to the herbicide LIBERTY™. We expect that the PAT gene under the control of RUBQ2 will be expressed and confer resistance on the transgenic plants. It is also expected that the PAT gene under the control of the other rice ubiquitin promoters would also be expressed in transgenic rice plants. Additionally, other herbicide-resistant genes could be used to produce the chimeric gene for insertion into the rice plants.

EXAMPLE 7
Fusion of Rice Ubiquitin Promoters with an Antifungal Coding Sequence The promoter isolated from RUBQ2 will be fused to a gene known to convey resistance to fungal growth. For example, both a chitinase gene (Dr. Muthukrishnan, Department of Biochemistry, Kansas State University) and the glucanase gene (from the public gene bank for Arabinopsis) will be used to develop rice plants with increased resistance to sheath blight, caused by the fungus *Rhizoctonia solani*. A plasmid containing a chimeric gene of the RUBQ2 promoter and the chosen structural coding sequence will be made according to the procedure in Example 2. This plasmid will be transferred by particle bombardment into rice cells from which transgenic rice plants will be grown as in Examples 3 and 4. The trangenic rice plants will then be grown. The grown rice plants will be innoculated with fungus and evaluated for resistance as compared to nontransgenic rice plants. We expect that the anti-fungal gene under the control of RUBQ2 will be expressed and confer resistance to the fungus on the transgenic plants. It is also expected that the anti-fungal gene under the control of the other three rice ubiquitin promoters would also be expressed in transgenic rice plants. Additionally, other anti-fungal genes could be used to produce the chimeric gene for insertion into the rice plants.

EXAMPLE 8
Fusion of Rice Ubiquitin Promoters with an Insect-resistant Coding Sequence The promoter isolated from RUBQ2 will be fused to a gene known to convey resistance to insect pests of rice, for example, the rice water weevil. Specifically, the CryIIIA gene will be isolated from *Bacillus thuringiensis*. Similar genes isolated from *Bacillius thuringiensis* have been used to generate transgenic plants of corn, potato, and cotton that show increased resistance to insect pests. A plasmid containing the chimeric gene of the RUBQ2 promoter and the CryIIIA gene will made according to the procedure in Example 2. This plasmid will be transferred by particle bombardment into rice cells from which transgenic rice plants will be grown as in Examples 3 and 4. The trangenic rice plants will then be grown. The mature rice plants will be evaluated for resistance to the insect pest, rice water weevil, as compared to nontransgenic rice plants. It is expected that the insect-resistant gene under the control of RUBQ2 will be expressed and confer resistance to insect pests on the transgenic plants. It is also expected that the CryIIIA gene under the control of the other three rice ubiquitin promoters would also be expressed in transgenic rice plants. Additionally, other insect-resistant genes could be used to produce the chimeric gene for insertion into the rice plants.

The complete disclosures of all references cited in this specification are hereby incorporated by reference. In the event of an otherwise irreconcilable conflict, however, the present specification shall control.

We claim:

1. An isolated nucleotide sequence comprising a rice ubiquitin promoter capable of controlling constitutive expression of a nucleic acid encoding a polypeptide, wherein said nucleotide sequence comprises at least a portion of SEQ ID NO:3 which is upstream of position 2785 and wherein said portion retains promoter activity.

2. A plasmid comprising the nucleotide sequence of claim 1.

3. A plant cell comprising the plasmid of claim 2.

4. A plant comprising the nucleotide sequence of claim 1 operatively linked to a heterologous nucleic acid sequence encoding a polypeptide.

5. A plant rice cell comprising the plasmid of claim 2.

6. A method of expressing a heterologous nucleic acid sequence encoding a polypeptide in a plant or in its progeny, comprising the steps of:

(a) transforming one or more plant cells with said heterologous nucleic acid sequence encoding the polypeptide wherein said nucleic acid sequence is operatively linked to the rice ubiquitin promoter of claim 1; and (b) regenerating a plant from the transformed plant cells, wherein the plant or its progeny expresses said heterologous nucleic acid sequence encoding the polypeptide.

7. A nucleic acid construct comprising the nucleotide sequence of claim 1 operatively linked to a heterologous nucleic acid sequence encoding a polypeptide.

8. The nucleic acid construct as recited in claim 7, wherein the heterologous nucleic acid sequence encoding a polypeptide is the polynucleotide encoding phosphinothrycin acetyl transferase.

9. The nucleic acid construct as recited in claim 7, wherein the heterologous nucleic acid sequence encoding a polypeptide is the polynucleotide encoding chitinase.

10. The nucleic acid construct as recited in claim 7, wherein the heterologous nucleic acid sequence encoding a polypeptide is the polynucleotide encoding glucanase.

11. A nucleic acid construct as recited in claim 7, wherein the heterologous nucleic acid sequence encoding a polypeptide is the polynucleotide encoding CryIIIA.

12. The plant according to claim 4, which is a rice plant.

* * * * *

SEQUENCE LISTING

<160> NUMBER OF SEQ ID NOS: 18

<210> SEQ ID NO 1
<211> LENGTH: 3184
<212> TYPE: DNA
<213> ORGANISM: Oryza sativa
<220> FEATURE:
<221> NAME/KEY: CDS
<222> LOCATION: (1702)..(3072)

<400> SEQUENCE: 1

```
gtcgacctga tgattatttt gttgatcatg attttctttt ggctatttga ttttttgaaa      60 gatattttt tccctgggaa gacacctatg ggacgaagat attatgttat atatatatat     120
atatatatat atatatatat atatatatat atatatatat atatatcaca tcagtctctg     180
cacaaagtgc atcctgggct gcttcaatta taaagcccca ttcaccacat ttgcgagata     240
gtcgaaaagc accatcaata ttgagcttca ggtattttg gttgtgttgt ggttggattg      300
agtccgatat ataccaaatc aatataattc actacggaat ataccatagc catcacaact     360
ttattaattt tggtagctta agatggtata tataataacc aattaacaac tgattctaat     420
tttactacgg cccagtatct accaatacaa acaacgagt atgttttctt ccgtcgtaat      480
cgtacacagt acaaaaaaac ctggccagcc tttcttgggc tgggctctc tttcgaaagg     540 tcacaaaacg tacacggcag taacgccctt cgctgcgtgt taacggccac caaccccgcc     600
gtgacgaaac ggcatcagct ttccacctcc tcgatatctc cgcggcgccg tctggacccg     660
cccccttccc gttcctttct ttccttctcg cgtttgcgtg gtggggacgg actccccaaa     720
ccgcctctcc ctctctttat ttgtctatat tctcactggg ccccacccac cgcaccctg     780 ggcccactca cgagtcccc cctcccgacc tataataacc ccaccccctc ctcgcctctt     840
cctccatcaa tcgaatcccc aaaatcgcag agaaaaaaa atctccctc gaagcgaagc     900 gtcgaatcgc cttctcaagg tatgcgattt tctgatcctc tccgttcctc gcgtttgatt     960
tgatttcccg gcctgttcgt gattgtgaga tgttgtggtt agtctccgtt ttgcgatctg    1020
tggtagattt gaacagggtt agatgggggtt cgcgtggtat gctggatctg tgattatgag    1080
cgatgctgaa cgtggtccaa gtattgattg gttcggatct agaagtagaa gtagaactgt    1140 gctaggggttg tgatttgttc cgatctgttc aatcagtagg atttagtctc tgttttctc    1200 gttgagccaa gtagcagcgt caggtatatt ttgcttaggt tgttttgat tcagtccctc    1260 tagttgcata gattctactc tgttcatgtt taatctaagg gctgcgtctt gttgattagt    1320
gattacatag catagctgtc aggatatttt acttgcttat gcctatctta tcaactgttg    1380
cacctgtaaa ttctagccta tgttaattaa cctgccttat gtgctctcgg gatagtgcta    1440
gtagttattg aatcagttg ccgatggaat tctagtagtt catagacctg cagattattt    1500
ttgtgaactc gagcacggtg cgtctctcta ttttgttagg tcactgttgg tgttgatagg    1560
```

-continued

```
tacactgatg ttattgtggt ttagatcgtg tatctaacat attggaataa tttgattgac    1620
tgatttctgc tgtacttgct tggtattgtt ataatttcat gttcatagtt gctgaccatg    1680
cttcggtaat tgtgtgtgca g atg cag atc ttt gtg aag acc ctc acc ggc     1731
                         Met Gln Ile Phe Val Lys Thr Leu Thr Gly
                          1               5                  10 aag acc atc acc ctc gag gtt gag tcc tcg gac acc att gac aat gtc     1779
Lys Thr Ile Thr Leu Glu Val Glu Ser Ser Asp Thr Ile Asp Asn Val
             15                  20                  25 aag gcc aag atc cag gac aag gag ggc atc ccc ccg gac cag cag cgt     1827
Lys Ala Lys Ile Gln Asp Lys Glu Gly Ile Pro Pro Asp Gln Gln Arg
         30                  35                  40 ctc atc ttc gct ggc aag cag ctt gag gat ggc cgc acc ctg gcc gac     1875
Leu Ile Phe Ala Gly Lys Gln Leu Glu Asp Gly Arg Thr Leu Ala Asp
     45                  50                  55 tac aac atc cag aag gag tcc acc ctc cac ctt gtg ctc agg ctc agg     1923
Tyr Asn Ile Gln Lys Glu Ser Thr Leu His Leu Val Leu Arg Leu Arg
 60                  65                  70 gga ggc atg cag atc ttc gtc aag acc ttg act ggc aag acc atc acc     1971
Gly Gly Met Gln Ile Phe Val Lys Thr Leu Thr Gly Lys Thr Ile Thr
 75                  80                  85                  90 ctt gag gtc gag tcg tct gac acc att gac aat gtc aag gcc aag atc     2019
Leu Glu Val Glu Ser Ser Asp Thr Ile Asp Asn Val Lys Ala Lys Ile
                 95                 100                 105 cag gac aag gag ggc atc ccc ccg gac cag cag cgt ctc atc ttc gct     2067
Gln Asp Lys Glu Gly Ile Pro Pro Asp Gln Gln Arg Leu Ile Phe Ala
             110                 115                 120 ggc aag cag ctt gag gat ggc cgc acc ctg gct gac tac aac atc cag     2115
Gly Lys Gln Leu Glu Asp Gly Arg Thr Leu Ala Asp Tyr Asn Ile Gln
         125                 130                 135 aag gag tcc acc ctc cac ctt gtg ctc agg ctc agg gga ggc atg cag     2163
Lys Glu Ser Thr Leu His Leu Val Leu Arg Leu Arg Gly Gly Met Gln
     140                 145                 150 atc ttc gtc aag acc ttg act ggc aag acc atc acc ctc gag gtc gag     2211
Ile Phe Val Lys Thr Leu Thr Gly Lys Thr Ile Thr Leu Glu Val Glu
155                 160                 165                 170 tcg tct gac acc att gac aat gtc aag gcc aag atc cag gac aag gag     2259
Ser Ser Asp Thr Ile Asp Asn Val Lys Ala Lys Ile Gln Asp Lys Glu
                 175                 180                 185 ggc atc ccc cca gac cag cag cgt ctc atc ttc gcc ggc aag cag ctg     2307
Gly Ile Pro Pro Asp Gln Gln Arg Leu Ile Phe Ala Gly Lys Gln Leu
             190                 195                 200 gag gat ggc cgc acc ctt gct gac tac aac atc cag aag gag tcc acc     2355
Glu Asp Gly Arg Thr Leu Ala Asp Tyr Asn Ile Gln Lys Glu Ser Thr
         205                 210                 215 ctc cac ctt gtg ctc agg ctc agg gga ggt atg cag atc ttc gtc aag     2403
Leu His Leu Val Leu Arg Leu Arg Gly Gly Met Gln Ile Phe Val Lys
     220                 225                 230 acc ctg acc ggc aag acc atc acc ctc gag gtc gag tcc tcg gac acg     2451
Thr Leu Thr Gly Lys Thr Ile Thr Leu Glu Val Glu Ser Ser Asp Thr
235                 240                 245                 250 atc gac aat gtg aaa gcc aag atc cag gac aag gag ggc atc ccc ccg     2499
Ile Asp Asn Val Lys Ala Lys Ile Gln Asp Lys Glu Gly Ile Pro Pro
                 255                 260                 265 gac cag cag cgt ctc atc ttt gct ggc aag cag ctg gag gat ggc cgc     2547
Asp Gln Gln Arg Leu Ile Phe Ala Gly Lys Gln Leu Glu Asp Gly Arg
             270                 275                 280 acc ctt gcc gac tac aac atc cag aag gag tcc acc ctc cac ctt gtg     2595
Thr Leu Ala Asp Tyr Asn Ile Gln Lys Glu Ser Thr Leu His Leu Val
         285                 290                 295
```

```
ctc agg ctc agg ggt ggt atg cag atc ttc gtc aag acc ctg acc ggc    2643
Leu Arg Leu Arg Gly Gly Met Gln Ile Phe Val Lys Thr Leu Thr Gly
300                 305                 310 aag acc atc acg ctt gag gtc gag tcc tcg gac acg atc gac aat gtg    2691
Lys Thr Ile Thr Leu Glu Val Glu Ser Ser Asp Thr Ile Asp Asn Val
315                 320                 325                 330 aag gcc aag atc cag gac aag gag ggt atc ccc ccg gac cag cag cgt    2739
Lys Ala Lys Ile Gln Asp Lys Glu Gly Ile Pro Pro Asp Gln Gln Arg
                335                 340                 345 ctc atc ttc gcc ggc aag cag ctt gag gat ggc cgc acc ttg gct gac    2787
Leu Ile Phe Ala Gly Lys Gln Leu Glu Asp Gly Arg Thr Leu Ala Asp
            350                 355                 360 tac aac atc cag aag gag tcc acc ctt cac ctg gtt ctc agg ctc agg    2835
Tyr Asn Ile Gln Lys Glu Ser Thr Leu His Leu Val Leu Arg Leu Arg
        365                 370                 375 ggt ggg atg cag atc ttc gtg aag acc ctg act ggc aag acc att acc    2883
Gly Gly Met Gln Ile Phe Val Lys Thr Leu Thr Gly Lys Thr Ile Thr
380                 385                 390 ctt gag gtt gag tcg tcc gac act att gac aac gtg aag gcg aag atc    2931
Leu Glu Val Glu Ser Ser Asp Thr Ile Asp Asn Val Lys Ala Lys Ile
395                 400                 405                 410 cag gac aag gag ggc atc ccc ccg gac cag cag cgt ctg atc ttt gct    2979
Gln Asp Lys Glu Gly Ile Pro Pro Asp Gln Gln Arg Leu Ile Phe Ala
                415                 420                 425 ggt aag cag ctt gag gat ggc cgc acc ttg gcg gat tac aac atc cag    3027
Gly Lys Gln Leu Glu Asp Gly Arg Thr Leu Ala Asp Tyr Asn Ile Gln
            430                 435                 440 aag gag tcc aca ctc cac ctg gtt ctg cgc ctc cgt ggt ggc cag        3072
Lys Glu Ser Thr Leu His Leu Val Leu Arg Leu Arg Gly Gly Gln
        445                 450                 455 taagtcctca gccatggagc tgctgctgtt ctagggttca caagtctgcc tattgtctcc  3132
caatggagct atggttgtct ggtctggtcc ttggtcgtgt cccgtttcat tg          3184
```

<210> SEQ ID NO 2
<211> LENGTH: 457
<212> TYPE: PRT
<213> ORGANISM: Oryza sativa

<400> SEQUENCE: 2

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140
```

```
Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
            165                 170                 175

Asn Val Lys Ala Lys Ile Gln Asp Lys Glu Gly Ile Pro Pro Asp Gln
                180                 185                 190

Gln Arg Leu Ile Phe Ala Gly Lys Gln Leu Glu Asp Gly Arg Thr Leu
            195                 200                 205

Ala Asp Tyr Asn Ile Gln Lys Glu Ser Thr Leu His Leu Val Leu Arg
210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
            245                 250                 255

Lys Ile Gln Asp Lys Glu Gly Ile Pro Pro Asp Gln Gln Arg Leu Ile
                260                 265                 270

Phe Ala Gly Lys Gln Leu Glu Asp Gly Arg Thr Leu Ala Asp Tyr Asn
            275                 280                 285

Ile Gln Lys Glu Ser Thr Leu His Leu Val Leu Arg Leu Arg Gly Gly
290                 295                 300

Met Gln Ile Phe Val Lys Thr Leu Thr Gly Lys Thr Ile Thr Leu Glu
305                 310                 315                 320

Val Glu Ser Ser Asp Thr Ile Asp Asn Val Lys Ala Lys Ile Gln Asp
            325                 330                 335

Lys Glu Gly Ile Pro Pro Asp Gln Gln Arg Leu Ile Phe Ala Gly Lys
                340                 345                 350

Gln Leu Glu Asp Gly Arg Thr Leu Ala Asp Tyr Asn Ile Gln Lys Glu
            355                 360                 365

Ser Thr Leu His Leu Val Leu Arg Leu Arg Gly Gly Met Gln Ile Phe
370                 375                 380

Val Lys Thr Leu Thr Gly Lys Thr Ile Thr Leu Glu Val Glu Ser Ser
385                 390                 395                 400

Asp Thr Ile Asp Asn Val Lys Ala Lys Ile Gln Asp Lys Glu Gly Ile
            405                 410                 415

Pro Pro Asp Gln Gln Arg Leu Ile Phe Ala Gly Lys Gln Leu Glu Asp
                420                 425                 430

Gly Arg Thr Leu Ala Asp Tyr Asn Ile Gln Lys Glu Ser Thr Leu His
            435                 440                 445

Leu Val Leu Arg Leu Arg Gly Gly Gln
    450                 455
```

<210> SEQ ID NO 3
<211> LENGTH: 4442
<212> TYPE: DNA
<213> ORGANISM: Oryza sativa
<220> FEATURE:
<221> NAME/KEY: CDS
<222> LOCATION: (2786)..(4159)

<400> SEQUENCE: 3

```
ctgcagaaat gcaaatttca taaaacaaac tactagtact gtttgttcat tggtcttatc      60
caaaacttag ccactgcaac aagttcttga accttagcac aatcatattg tgcatgcact     120
tgtttattgc aaagaatggt gcgtagggaa cacgcatgat ttttgaattg ctggcacata     180
attttatcat tagaaactgg aatgcaacat gtacccttg tcatggtttc tttccgagac      240
```

-continued

```
attgcactgt ttttttttaat cctatcatta tcataatgcc aagaactggt caccaaccag    300
cattttgcat catggttagt tgagctgtcc ccatgtatca ataggtgcat tgtattggtc    360
caaaatataa atgcagtgga tgcaacctat ctcatggccg tcaacaaaag aaatcaaaag    420
ggaaatgcac catcttatat ctccagttta tatgaacaga ttggataaga tcataagatc    480
aagtggttta tattattttg aggaatataa catggattca tcctaatcac tcgtctaggc    540
agtatgtgta ttcatgatgg atatggtact atactacgga gttttttctt cacaaaataa    600
cctgttattt tgacctccaa ccaaacacga attataccaa aaattgggtt atttcatcta    660
tagtacaact ctattataaa catgcagtaa attatcctac acatatacca aaattcaagt    720
gtaataatcc taatacacag acttaaaaat caaactattt cctttttaag atatggaaaa    780
ccattttttt aacggaagga aaacaaattc gggtcaaggc ggaagccagc gcgccacccc    840
acgtcagcga atacggaggc gcggggttga cggcgtcacc cggtcctaac ggcgaccaac    900
aaaccagcca gaagaaatta cagtaaaaaa aagtaaattg cactttgacc caccttttat    960
tacccaaagt ttcaatttgg accacccctta acctatctt ttcaaattgg gccgggttgt   1020
ggtttggact accatgaaca acttttcgtc atgtctaact tcccctttcgg caaacatatg   1080
aaccatatat agaggagatc ggccgtatac tagagctgat gtgtttaagg tcgttgattg   1140
cacgagaaaa aaaaatccaa atcgcaacaa tagcaaattt atctagttca aagtgaaaag   1200
atatgtttaa aggtagtcca aagtaaaact taggggctgt ttggttccca gccatacttt   1260
accattactt gccaacaaaa gttgccacac cttgtctaag gtgaggtgat caaattgtta   1320
gccacaactt actaagccta agggaatctt gccacacttt tttgagccat tgacacgtgg   1380
gacttaattt gttagaggga aatcttgcca caactgtggc tacaaccaaa cacctgtcaa   1440
atttgcctaa cctaggcgt ggcaaactgt ggcaaagtgt ggcttacaac caaacacacc   1500
cttagataat aaaatgtggt ccaaagcgta attcactaaa aaaaaatcaa cgagacgtgt   1560
accaaacgga gacaaacggc atcttctcga aatttcccaa ccgctggctg gcccgcctcg   1620
tcttcccgga aaccgcggtg gtttcagcgt ggcggattct ccaagcagac ggagacgtca   1680
cggcacggac tcctcccacc acccaaccgc cataaatacc agcccctca tctcctctcc   1740
tcgcatcagc tccacccccg aaaaatttct ccccaatctc gcgaggctct cgtcgtcgaa   1800
tcgaatcctc tcgcgtcctc aaggtacgct gcttctcctc tcctcgcttc gtttcgattc   1860
gatttcggac gggtgaggtt gttttgttgc tagatccgat tggtggttag ggttgtcgat   1920
gtgattatcg tgagatgttt aggggttgta gatctgatgg ttgtgatttg ggcacggttg   1980
gttcgatagg tggaatcgtg gttaggtttt gggattggat gttggttctg atgattgggg   2040
ggaattttta cggttagatg aattgttgga tgattcgatt ggggaaatcg gtgtagatct   2100
gttggggaat tgtggaacta gtcatgcctg agtgattggt gcgatttgta gcgtgttcca   2160
tctagtaggc cttgttgcga gcatgttcag atctactgtt ccgctcttga ttgagttatt   2220
ggtgccatgt gtgggtgcaa acacaggctg caatatgtta tatctgtttt gtgtttgatg   2280
tagatctgta gggtagttct tcttagacat ggttcaatta tgtagcttgt cgtttcgatt   2340
tgatgctcat atgttcacag attagataat gatgaactct tttaattaat tgtcaatggt   2400
aaataggaag tcttatcgct atatctgtca taatgatctc atgttactat ctgccagtaa   2460
tttatgctaa gcactatatt agaatatcat gttacaatct gtagtaatat catgttacaa   2520
tctgtagttc atctatataa tctattgtgg taatttcttt ttactatctg tgtgaagatt   2580
```

-continued

```
attgccacta gttcattcta cttatttctg aagttcagga tacgtgtgct gttactacct    2640
atctgaatac atgtgtgatg tgcctgttac tatcttttg aatacatgta tgttctgttg     2700
gaatatgttt gctgtttgat ccgttgttgt gtccttaatc ttgtgctagt tcttacccta    2760
tctgtttggt gattatttct tgcag atg cag atc ttt gtg aag aca ttg acc      2812
                             Met Gln Ile Phe Val Lys Thr Leu Thr
                              1               5 ggc aag act atc acc ctc gag gtg gag tcc tct gac acc atc gat aat      2860
Gly Lys Thr Ile Thr Leu Glu Val Glu Ser Ser Asp Thr Ile Asp Asn
 10              15                  20                  25 gtc aag gct aag atc caa gat aag gag ggc atc ccc ccg gac cag cag      2908
Val Lys Ala Lys Ile Gln Asp Lys Glu Gly Ile Pro Pro Asp Gln Gln
         30                  35                  40 cgt ctc atc ttc gct ggc aag cag ctg gag gat ggc agg acc ctt gct      2956
Arg Leu Ile Phe Ala Gly Lys Gln Leu Glu Asp Gly Arg Thr Leu Ala
             45                  50                  55 gac tac aac atc cag aag gag tcg acc ctt cac ctt gtc ctc cgc ctc      3004
Asp Tyr Asn Ile Gln Lys Glu Ser Thr Leu His Leu Val Leu Arg Leu
         60                  65                  70 cgt ggt ggc atg cag atc ttt gtc aag act ctg acc ggc aag act atc      3052
Arg Gly Gly Met Gln Ile Phe Val Lys Thr Leu Thr Gly Lys Thr Ile
 75                  80                  85 acc ctt gag gtg gag tct tct gac acc atc gac aac gtc aag gcc aag      3100
Thr Leu Glu Val Glu Ser Ser Asp Thr Ile Asp Asn Val Lys Ala Lys
 90                  95                 100                 105 atc cag gac aaa gag ggc atc ccc cca gac cag cag cgt ctc atc ttc      3148
Ile Gln Asp Lys Glu Gly Ile Pro Pro Asp Gln Gln Arg Leu Ile Phe
                110                 115                 120 gcc ggc aag cag ctg gag gat ggc agg acc ctt gct gac tac aac atc      3196
Ala Gly Lys Gln Leu Glu Asp Gly Arg Thr Leu Ala Asp Tyr Asn Ile
             125                 130                 135 cag aag gag tcc acc ctc cac ctt gtc ctc cgc ctc cgt ggt ggc atg      3244
Gln Lys Glu Ser Thr Leu His Leu Val Leu Arg Leu Arg Gly Gly Met
         140                 145                 150 cag atc ttt gtc aag aca ctg acc ggc aag acc atc acc ctc gag gtg      3292
Gln Ile Phe Val Lys Thr Leu Thr Gly Lys Thr Ile Thr Leu Glu Val
 155                 160                 165 gaa tct tct gac acc atc gac aac gtc aag gcc aag atc cag gac aag      3340
Glu Ser Ser Asp Thr Ile Asp Asn Val Lys Ala Lys Ile Gln Asp Lys
170                 175                 180                 185 gag ggc att ccc ccg gac cag cag cgt ctc atc ttt gcc ggc aag cag      3388
Glu Gly Ile Pro Pro Asp Gln Gln Arg Leu Ile Phe Ala Gly Lys Gln
                190                 195                 200 ctt gag gac ggc agg acc ctt gct gac tac aac atc cag aag gag tca      3436
Leu Glu Asp Gly Arg Thr Leu Ala Asp Tyr Asn Ile Gln Lys Glu Ser
             205                 210                 215 acg ctt cac ctt gtc ctc cgt ctc agg gga ggc atg caa atc ttc gtg      3484
Thr Leu His Leu Val Leu Arg Leu Arg Gly Gly Met Gln Ile Phe Val
         220                 225                 230 aag act ctg acc ggc aag acc atc acc ctc gag gtg gag tct tct gat      3532
Lys Thr Leu Thr Gly Lys Thr Ile Thr Leu Glu Val Glu Ser Ser Asp
 235                 240                 245 acc atc gac aat gtc aag gcc aag atc cag gac aag gag ggc att ccc      3580
Thr Ile Asp Asn Val Lys Ala Lys Ile Gln Asp Lys Glu Gly Ile Pro
250                 255                 260                 265 ccg gac cag cag cgc ctc atc ttt gct ggc aag cag ctg gag gat ggc      3628
Pro Asp Gln Gln Arg Leu Ile Phe Ala Gly Lys Gln Leu Glu Asp Gly
                270                 275                 280 agg acc ctt gct gac tac aac atc cag aag gag tcc acc ctc cac ctt     3676
```

```
                                                                              -continued Arg Thr Leu Ala Asp Tyr Asn Ile Gln Lys Glu Ser Thr Leu His Leu
            285                 290                 295 gtg ctc cgc ctt cgt ggt ggt atg cag atc ttt gtc aag acc ctc aca      3724
Val Leu Arg Leu Arg Gly Gly Met Gln Ile Phe Val Lys Thr Leu Thr
        300                 305                 310 ggc aag acc atc acc ctg gag gtt gag agc tcg gac acc atc gac aac      3772
Gly Lys Thr Ile Thr Leu Glu Val Glu Ser Ser Asp Thr Ile Asp Asn
    315                 320                 325 gtc aag gcc aag atc cag gac aag gag ggc atc ccc cca gac cag cag      3820
Val Lys Ala Lys Ile Gln Asp Lys Glu Gly Ile Pro Pro Asp Gln Gln
330                 335                 340                 345 cgt ctc atc ttc gcc ggc aag cag ctc gag gat ggc cgc acc ctt gcc      3868
Arg Leu Ile Phe Ala Gly Lys Gln Leu Glu Asp Gly Arg Thr Leu Ala
                350                 355                 360 gac tac aac atc cag aag gag tct acc ctc cac ctg gtg ctt cgt ctc      3916
Asp Tyr Asn Ile Gln Lys Glu Ser Thr Leu His Leu Val Leu Arg Leu
            365                 370                 375 cgt ggt ggt atg cag atc ttc gtg aag acc ttg act ggg aag acc atc      3964
Arg Gly Gly Met Gln Ile Phe Val Lys Thr Leu Thr Gly Lys Thr Ile
        380                 385                 390 act ttg gag gtt gag agc tcc gac acc att gat aat gtg aag gcc aag      4012
Thr Leu Glu Val Glu Ser Ser Asp Thr Ile Asp Asn Val Lys Ala Lys
    395                 400                 405 atc cag gac aag gag ggg att ccc cca gac cag cag cgt ctg atc ttc      4060
Ile Gln Asp Lys Glu Gly Ile Pro Pro Asp Gln Gln Arg Leu Ile Phe
410                 415                 420                 425 gct ggc aag cag ctg gag gat gga cgc acc ctc gcc gac tac aac atc      4108
Ala Gly Lys Gln Leu Glu Asp Gly Arg Thr Leu Ala Asp Tyr Asn Ile
                430                 435                 440 cag aag gag tcc acc ctc cac ctg gtg ctc cgc ctc cgt ggt ggt cag      4156
Gln Lys Glu Ser Thr Leu His Leu Val Leu Arg Leu Arg Gly Gly Gln
            445                 450                 455 taa tcagccagtt tggtggagct gccgatgtgc ctggtcatcc cgagcctctg           4209
ttcgtcaagt atttgtggtg ctgatgtcta cttgtgtctg gtttaatgga ccatcgagtc    4269
cgtatgatat gttagtttta tgaaacagtt tcctgtggga cagcagtatg ctttatgaat    4329
aagttggatt tgaacctaaa tatgtgctca atttgctcat ttgcatctca ttcctgttga    4389
tgttttattt gagttgcaag tttgaaaatg ctgcatattc ttattaaacg gca           4442

<210> SEQ ID NO 4
<211> LENGTH: 457
<212> TYPE: PRT
<213> ORGANISM: Oryza sativa

<400> SEQUENCE: 4

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95
```

-continued

```
Asp Thr Ile Asp Asn Val Lys Ala Lys Ile Gln Asp Lys Glu Gly Ile
            100                 105                 110
Pro Pro Asp Gln Gln Arg Leu Ile Phe Ala Gly Lys Gln Leu Glu Asp
        115                 120                 125
Gly Arg Thr Leu Ala Asp Tyr Asn Ile Gln Lys Glu Ser Thr Leu His
    130                 135                 140
Leu Val Leu Arg Leu Arg Gly Gly Met Gln Ile Phe Val Lys Thr Leu
145                 150                 155                 160
Thr Gly Lys Thr Ile Thr Leu Glu Val Glu Ser Ser Asp Thr Ile Asp
                165                 170                 175
Asn Val Lys Ala Lys Ile Gln Asp Lys Glu Gly Ile Pro Pro Asp Gln
            180                 185                 190
Gln Arg Leu Ile Phe Ala Gly Lys Gln Leu Glu Asp Gly Arg Thr Leu
        195                 200                 205
Ala Asp Tyr Asn Ile Gln Lys Glu Ser Thr Leu His Leu Val Leu Arg
    210                 215                 220
Leu Arg Gly Gly Met Gln Ile Phe Val Lys Thr Leu Thr Gly Lys Thr
225                 230                 235                 240
Ile Thr Leu Glu Val Glu Ser Ser Asp Thr Ile Asp Asn Val Lys Ala
                245                 250                 255
Lys Ile Gln Asp Lys Glu Gly Ile Pro Pro Asp Gln Gln Arg Leu Ile
            260                 265                 270
Phe Ala Gly Lys Gln Leu Glu Asp Gly Arg Thr Leu Ala Asp Tyr Asn
        275                 280                 285
Ile Gln Lys Glu Ser Thr Leu His Leu Val Leu Arg Leu Arg Gly Gly
    290                 295                 300
Met Gln Ile Phe Val Lys Thr Leu Thr Gly Lys Thr Ile Thr Leu Glu
305                 310                 315                 320
Val Glu Ser Ser Asp Thr Ile Asp Asn Val Lys Ala Lys Ile Gln Asp
                325                 330                 335
Lys Glu Gly Ile Pro Pro Asp Gln Gln Arg Leu Ile Phe Ala Gly Lys
            340                 345                 350
Gln Leu Glu Asp Gly Arg Thr Leu Ala Asp Tyr Asn Ile Gln Lys Glu
        355                 360                 365
Ser Thr Leu His Leu Val Leu Arg Leu Arg Gly Gly Met Gln Ile Phe
    370                 375                 380
Val Lys Thr Leu Thr Gly Lys Thr Ile Thr Leu Glu Val Glu Ser Ser
385                 390                 395                 400
Asp Thr Ile Asp Asn Val Lys Ala Lys Ile Gln Asp Lys Glu Gly Ile
                405                 410                 415
Pro Pro Asp Gln Gln Arg Leu Ile Phe Ala Gly Lys Gln Leu Glu Asp
            420                 425                 430
Gly Arg Thr Leu Ala Asp Tyr Asn Ile Gln Lys Glu Ser Thr Leu His
        435                 440                 445
Leu Val Leu Arg Leu Arg Gly Gly Gln
    450                 455
```

<210> SEQ ID NO 5
<211> LENGTH: 1846
<212> TYPE: DNA
<213> ORGANISM: Oryza sativa
<220> FEATURE:
<221> NAME/KEY: CDS
<222> LOCATION: (383)..(487)
<220> FEATURE:
<221> NAME/KEY: CDS

```
<222> LOCATION: (1154)..(1276)
<220> FEATURE:
<221> NAME/KEY: intron
<222> LOCATION: (488)..(1153)

<400> SEQUENCE: 5
```

| | |
|---|---:|
| aagctttgct ccgtgtctgc ttgggccata tacacggacc agcccaatag ccagaagcct | 60 |
| gtagctctcc atgggcccgt actcgtgcca cgtgtcaatc ctgtggttcg gtttcgtggc | 120 |
| ggttgcgttt cctcctctct cttttctttt tcatctttt ttttcttac gacatttata | 180 |
| ggtttcgtag cggctgcgtt tcctattttc cttttctttt tctatttatt tttatgggat | 240 |
| attcgctttc gtggcggctg cgtttcctcg cccatatata agagcgggtg accacgactg | 300 |
| cggcgcggcg caccactcca ccaccaccac caccactcca ccgatcggcg agagcgcggg | 360 |

```
gagatcgttc gacggcggca ag atg cag atc ttc gtg aag acg ctg acg ggg   412
                         Met Gln Ile Phe Val Lys Thr Leu Thr Gly
                          1               5                  10 aag acg atc acg ctg gag gtg gag agc agc gac acc atc gac aac gtc   460
Lys Thr Ile Thr Leu Glu Val Glu Ser Ser Asp Thr Ile Asp Asn Val
             15                  20                  25 aag gcc aag atc cag gac aag gaa ggt atgctcgcac cggccatggt          507
Lys Ala Lys Ile Gln Asp Lys Glu Gly
         30                  35
```

| | |
|---|---:|
| cgccgactcg ccgtctctcc attcctagcc ctccccgttc tcgctgacct gcattgattg | 567 |
| ctgctttgtt tggtgtgctc gatatgctga tatgttactg tgtttgtgtg caaatctgtg | 627 |
| ggtttagtgg agtttatgcg ctgtggatat agcagttgca agtttttgtg ggtttagtgg | 687 |
| aatactgagc aaaatgcgta aactctagta gtatcaccca tccaatgttg ctgcttttct | 747 |
| accatttttt tagatctgta acagagtaga tccatcttga aaagcgtata aaagcccaaa | 807 |
| accttccgat tgaatagttc ctttccaatt tctctggagg cgattttttt ttttataact | 867 |
| gtcacgctat actgcacggt taactagatc taaaaggtcc cctgttttcc tgttacaata | 927 |
| agcaaaaaaa gtatgttgtt ttataatctg attcgaacta cttgaataga ttcctaaaac | 987 |
| gttctgtatc cttttacatg ctgtattgat ttgatcctcc ggtagtgtta atttcatatc | 1047 |
| acgtctgct aagctggaaa ttgttgaatc cgtgtgtgcg catggtcgaa tctctctgct | 1107 |
| gtttaagctg atgaactgta tccatctctg cacaacccgt acag gt atc ccg ccg | 1162 |
| | Ile Pro Pro |

```
gac cag cag cgc ctc atc ttc gcc ggg aag cag ctg gaa gac ggc cgc   1210
Asp Gln Gln Arg Leu Ile Phe Ala Gly Lys Gln Leu Glu Asp Gly Arg
     40                  45                  50 acc ctg gcc gac tac aac atc cag aag gag tcg acg ctg cac ctg gtg   1258
Thr Leu Ala Asp Tyr Asn Ile Gln Lys Glu Ser Thr Leu His Leu Val
 55                  60                  65                  70 ctc cgc ctc cgc ggc ggc agcagggggcg gctacaccat ccaggagccc          1306
Leu Arg Leu Arg Gly Gly
                 75
```

| | |
|---|---:|
| accctccggg ctcttgcgct caagtacaga gagaagaaga aggtctgccg caagtacgaa | 1366 |
| ctcacgcacg ccccgcccg cccgcacctt gattccagat gatactagct ttgcatccgc | 1426 |
| ggctaacatg aactgatttg atttcaaccc tgttccatct cctaatgcag gtgctatgca | 1486 |
| cgccttccca tcaggtctca ccactgccgc aagaagaagt gtggccacag caaggaggtg | 1546 |
| agcatttcta aagttcctct tcgtatgtta acacaccatt gttcatgttc ttggctttgc | 1606 |
| tttggtctga atgctggaga tgaattttc ttagatagtt gtcatactcc tgtactttgt | 1666 |
| attggaaatt cgaaatcgtc attggttgcc tccgtgtgcg cttgtcacgg atttggaaat | 1726 |

```
ttggatagag tcgcatcagt ttgaacacca attcagttca gtggtttgcc ctttgaattg    1786
tgtttattct agtgattact gtgttctgca tcggttgcaa tacacgctgt acagtttttt    1846
```

<210> SEQ ID NO 6
<211> LENGTH: 76
<212> TYPE: PRT
<213> ORGANISM: Oryza sativa

<400> SEQUENCE: 6

```
Met Gln Ile Phe Val Lys Thr Leu Thr Gly Lys Thr Ile Thr Leu Glu
  1               5                  10                  15

Val Glu Ser Ser Asp Thr Ile Asp Asn Val Lys Ala Lys Ile Gln Asp
                 20                  25                  30

Lys Glu Gly Ile Pro Pro Asp Gln Gln Arg Leu Ile Phe Ala Gly Lys
             35                  40                  45

Gln Leu Glu Asp Gly Arg Thr Leu Ala Asp Tyr Asn Ile Gln Lys Glu
         50                  55                  60

Ser Thr Leu His Leu Val Leu Arg Leu Arg Gly Gly
     65                  70                  75
```

<210> SEQ ID NO 7
<211> LENGTH: 35
<212> TYPE: PRT
<213> ORGANISM: Oryza sativa

<400> SEQUENCE: 7

```
Met Gln Ile Phe Val Lys Thr Leu Thr Gly Lys Thr Ile Thr Leu Glu
  1               5                  10                  15

Val Glu Ser Ser Asp Thr Ile Asp Asn Val Lys Ala Lys Ile Gln Asp
                 20                  25                  30

Lys Glu Gly
         35
```

<210> SEQ ID NO 8
<211> LENGTH: 41
<212> TYPE: PRT
<213> ORGANISM: Oryza sativa

<400> SEQUENCE: 8

```
Ile Pro Pro Asp Gln Gln Arg Leu Ile Phe Ala Gly Lys Gln Leu Glu
  1               5                  10                  15

Asp Gly Arg Thr Leu Ala Asp Tyr Asn Ile Gln Lys Glu Ser Thr Leu
                 20                  25                  30

His Leu Val Leu Arg Leu Arg Gly Gly
             35                  40
```

<210> SEQ ID NO 9
<211> LENGTH: 1396
<212> TYPE: DNA
<213> ORGANISM: Oryza sativa
<220> FEATURE:
<221> NAME/KEY: CDS
<222> LOCATION: (592)..(696)
<220> FEATURE:
<221> NAME/KEY: CDS
<222> LOCATION: (1305)..(1394)
<220> FEATURE:
<221> NAME/KEY: intron
<222> LOCATION: (697)..(1304)

<400> SEQUENCE: 9

```
aagcttgtct gtctctacta gataccaggg tttcatcttt cggtttggtc atttggacca      60
gggtgcccga aatatcgaaa tttcagaaat ttcggttcga aattatatga attttttgaac    120 aaaatttgat taaattaaac aaaatattat cagatttgca aaaaatatga aaaaaaaatc    180
ggtcgaaata atgtcgtatc tgggttcgat ccgaaatttt gaacccatgc tagctgccag    240
gctttggatt ctgagcgtca cgtcaggcac aataaaatat ttgggcctct aactcttcgt    300
gggctgatct gggccgtagc agacgagaga gcccatgaca cgatctcatc aattccgtag    360
tggccacgga actcacgtag cgcaaatgcc gctcccgttt ccgcatcgtg cgatttatct    420
cctttctgtt tccgaatttt attagtagtt gcgatattat taatacaggt ctcgtagcgg    480
ccgcgtctcc tcctcccctta tataaaggca gcgtttctgc aagttattac ccaatctaca   540
cgagagagag atcgttcgac gcatatagag agagagagag atagaggcaa g atg cag      597
                                                          Met Gln
                                                            1 atc ttc gtg aag acg ctg acg ggg aag acg atc acg ctg gag gtg gag       645
Ile Phe Val Lys Thr Leu Thr Gly Lys Thr Ile Thr Leu Glu Val Glu
        5                  10                  15 agc agc gac acc atc gac aac gtc aag gcc aag atc cag gac aag gaa       693
Ser Ser Asp Thr Ile Asp Asn Val Lys Ala Lys Ile Gln Asp Lys Glu
    20                  25                  30 ggt aatataacac gatatcccta gcttcttcgt ttgcatgttc atcttgttta            746
Gly
35 atcgttgatg tcttgatgtc gtctcgcgat gatcgactgc acgtacgtac gccgtacatt     806 tgctggcatt gctcgtcccg ttaatttagt gactcatcct ttttttcgta cgtcgtgctc     866 ttgtgcgtct agacagtaga aatcatgtgt tttgcactag atgcgtggtg ggttgatact     926 gccgaaattg ttcaatattg tagttgtaga ttagatcgat ttgataacca aaaaggaagc     986 cttgtacttt tccattacat tacataggtc taagcatgcg tgtgtttagt cgcagtaagc    1046 acggagcaac aaatccaatc tagccatctg cttatagttc gtcttcgctg tgtacatgtt    1106 tctattctgt cttagtagtt taaaacgata tgctagtacc gtttatctct tgatagggag    1166 tgccttcatc gatgacattg ctgcataact gtaattaaag actcgttttt cttcgttttc    1226 atggattaat atttacttcc gagcccattc gactagctaa aactcattca tatctctttc    1286 actgttgtat atataggt atc cct ccg gac cag cag cgc ctc atc ttc gcg      1337
                    Ile Pro Pro Asp Gln Gln Arg Leu Ile Phe Ala
                                40                  45 ggg aag cag ctg gag gat ggc cgc acc ctg gcc gac tac aac atc cag      1385
Gly Lys Gln Leu Glu Asp Gly Arg Thr Leu Ala Asp Tyr Asn Ile Gln
        50                  55                  60 aag gag tcg ac                                                         1396
Lys Glu Ser
       65

<210> SEQ ID NO 10
<211> LENGTH: 65
<212> TYPE: PRT
<213> ORGANISM: Oryza sativa

<400> SEQUENCE: 10

Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
```

```
                35                  40                  45
Gln Leu Glu Asp Gly Arg Thr Leu Ala Asp Tyr Asn Ile Gln Lys Glu
    50                  55                  60
Ser
 65

<210> SEQ ID NO 11
<211> LENGTH: 35
<212> TYPE: PRT
<213> ORGANISM: Oryza sativa

<400> SEQUENCE: 11

Met Gln Ile Phe Val Lys Thr Leu Thr Gly Lys Thr Ile Thr Leu Glu
 1               5                  10                  15
Val Glu Ser Ser Asp Thr Ile Asp Asn Val Lys Ala Lys Ile Gln Asp
                20                  25                  30
Lys Glu Gly
        35

<210> SEQ ID NO 12
<211> LENGTH: 30
<212> TYPE: PRT
<213> ORGANISM: Oryza sativa

<400> SEQUENCE: 12

Ile Pro Pro Asp Gln Gln Arg Leu Ile Phe Ala Gly Lys Gln Leu Glu
 1               5                  10                  15
Asp Gly Arg Thr Leu Ala Asp Tyr Asn Ile Gln Lys Glu Ser
                20                  25                  30

<210> SEQ ID NO 13
<211> LENGTH: 14
<212> TYPE: DNA
<213> ORGANISM: Zea mays

<400> SEQUENCE: 13
ctggtcccct ccga                                                    14

<210> SEQ ID NO 14
<211> LENGTH: 14
<212> TYPE: DNA
<213> ORGANISM: Zea mays

<400> SEQUENCE: 14
ctcgagattc cgct                                                    14

<210> SEQ ID NO 15
<211> LENGTH: 15
<212> TYPE: DNA
<213> ORGANISM: Oryza sativa

<400> SEQUENCE: 15
ctcgatatct ccgcg                                                   15

<210> SEQ ID NO 16
<211> LENGTH: 15
<212> TYPE: DNA
<213> ORGANISM: Oryza sativa
```

-continued

```
<400> SEQUENCE: 16
ctggacccgc cccct                                              15

<210> SEQ ID NO 17
<211> LENGTH: 15
<212> TYPE: DNA
<213> ORGANISM: Drosophila melanogaster

<400> SEQUENCE: 17
ctggaatntt ctaga                                              15

<210> SEQ ID NO 18
<211> LENGTH: 10
<212> TYPE: DNA
<213> ORGANISM: Unknown
<220> FEATURE:
<223> OTHER INFORMATION: Description of Unknown Organism: PEA LEGUMIN

<400> SEQUENCE: 18
ggtgtggaaa                                                    10
```